ized">United States Patent [19]

Vogt et al.

[11] Patent Number: 5,429,727
[45] Date of Patent: Jul. 4, 1995

[54] ELECTROCATALYTIC CERMET GAS DETECTOR/SENSOR

[75] Inventors: Michael C. Vogt; Erika L. Shoemarker, both of Westmont, Ill.; Anthony V. Fraioli, deceased, late of Bristol, Vt., by Natelle B. Fraioli, executrix

[73] Assignee: ARCH Development Corporation, Chicago, Ill.

[21] Appl. No.: 129,964

[22] Filed: Sep. 30, 1993

[51] Int. Cl.[6] ............................................. G01N 27/26
[52] U.S. Cl. ........................ 204/153.14; 204/153.16; 204/153.18; 204/153.1; 204/425; 204/426; 204/427; 204/408; 204/412; 73/31.06
[58] Field of Search ............... 204/153.18, 424, 153.16, 204/425, 426, 427, 429, 153.1, 153.14, 412; 73/31.06

[56] References Cited
U.S. PATENT DOCUMENTS 2,965,842 12/1960 Jacobson ........................ 73/31.06
3,691,023 9/1972 Ruka et al. ..................... 204/425
3,860,498 1/1975 Jones .............................. 204/425
4,107,019 8/1978 Takao et al. .................... 204/426
4,264,425 4/1981 Kimura et al. .................. 204/425
4,300,991 11/1981 Chiba et al. .................... 204/425
4,378,691 4/1983 Terada et al. ................ 73/31.06
4,416,763 11/1983 Fujishiro ....................... 204/425

Primary Examiner—John Niebling
Assistant Examiner—Bruce F. Bell
Attorney, Agent, or Firm—Reinhart, Boerner, Van Deuren, Norris & Rieselbach

[57] ABSTRACT

An electrocatalytic device for sensing gases. The gas sensing device includes a substrate layer, a reference electrode disposed on the substrate layer comprised of a nonstoichiometric chemical compound enabling oxygen diffusion therethrough, a lower reference electrode coupled to the reference electrode, a solid electrolyte coupled to the lower reference electrode and an upper catalytically active electrode coupled to the solid electrolyte.

20 Claims, 23 Drawing Sheets

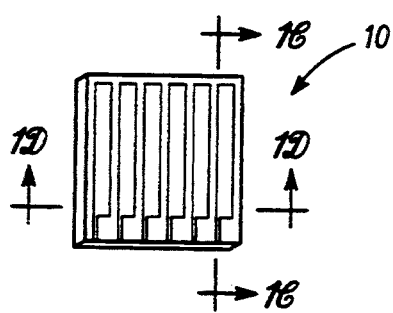
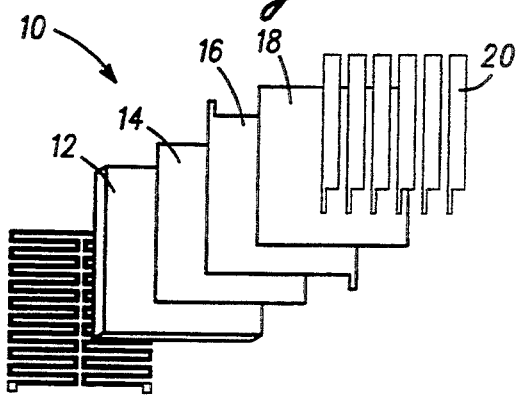
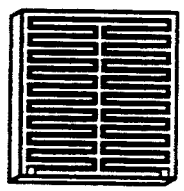
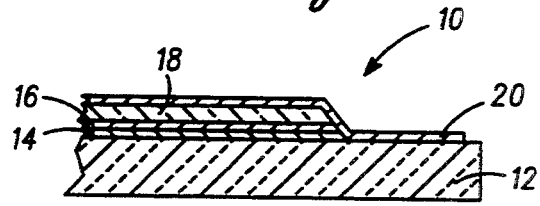
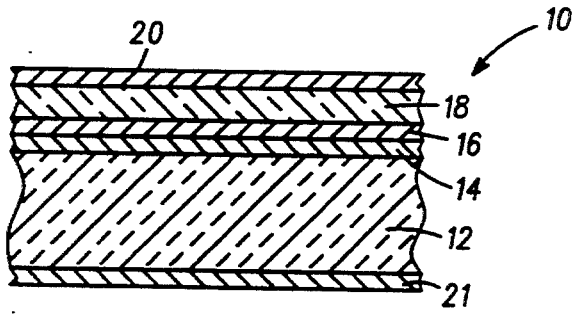
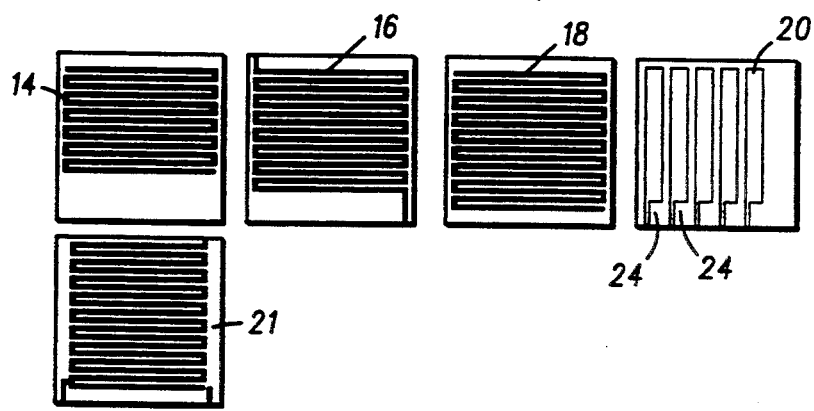

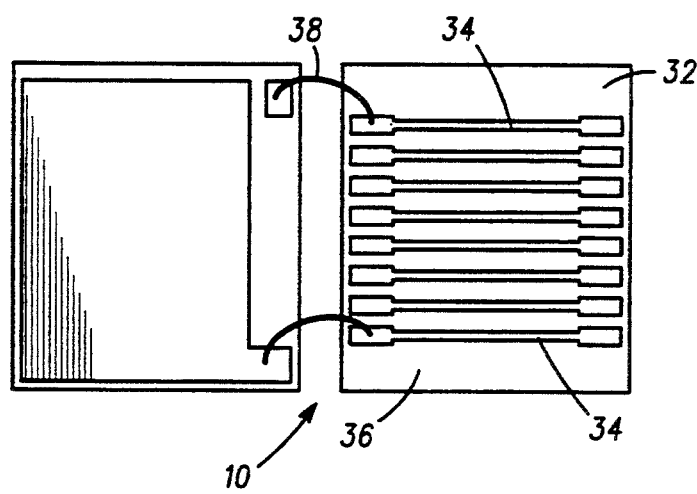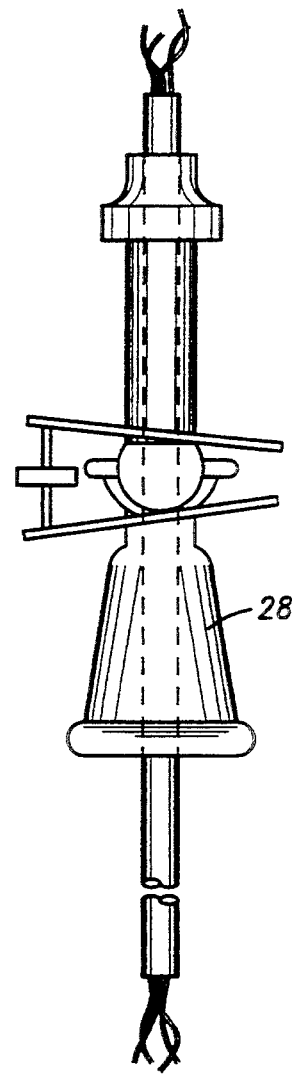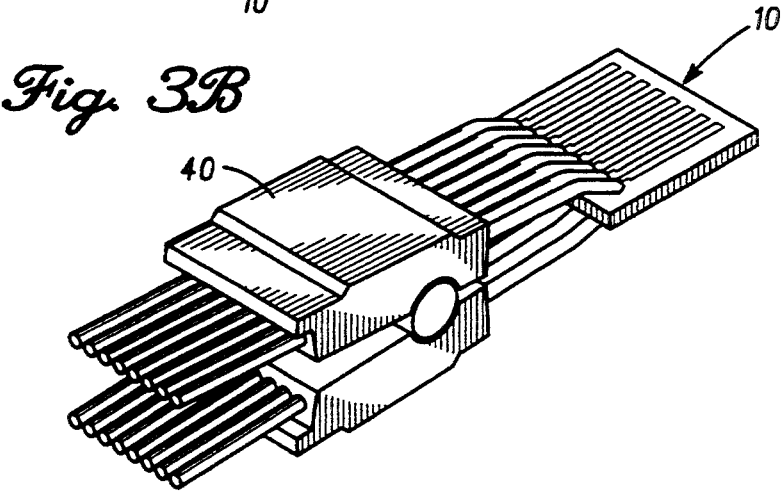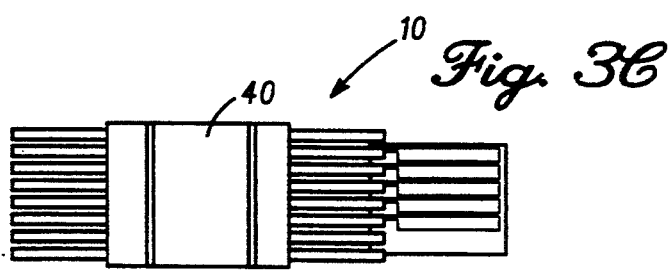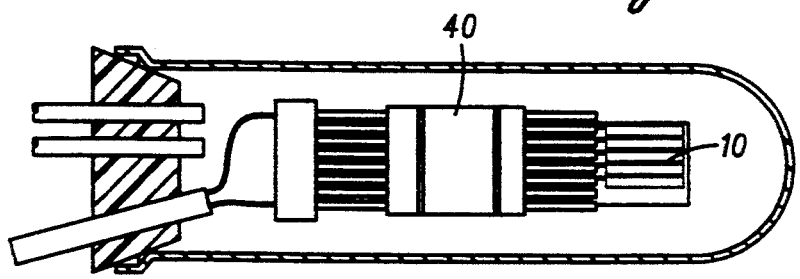

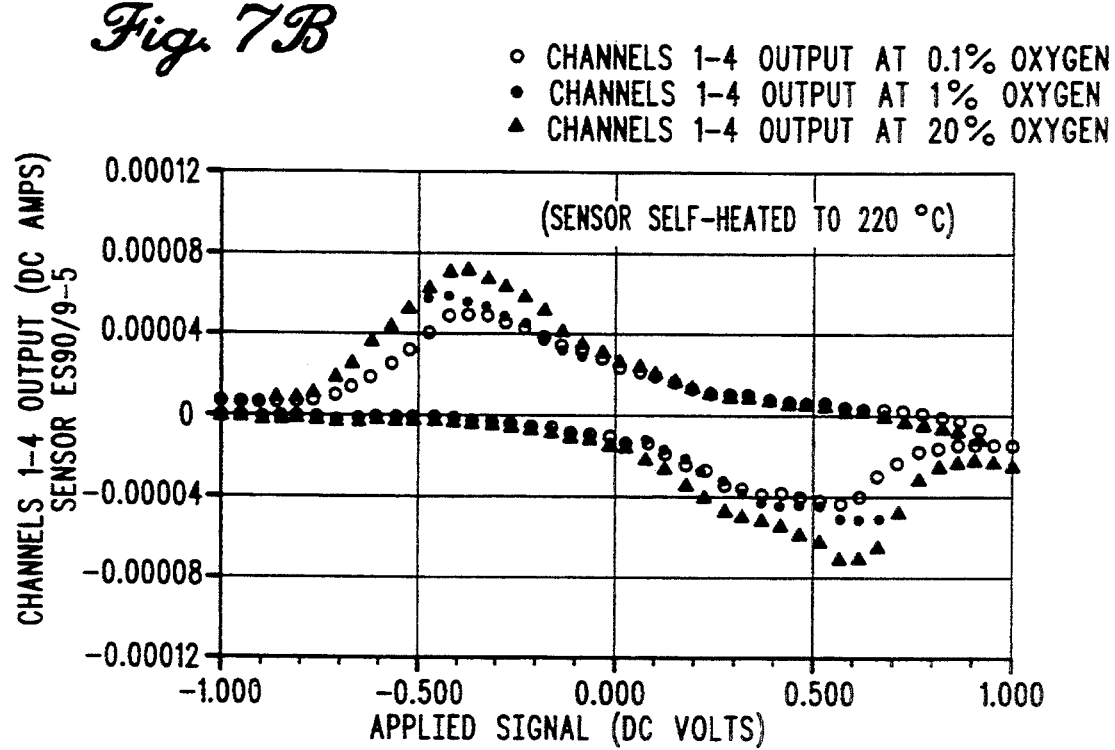
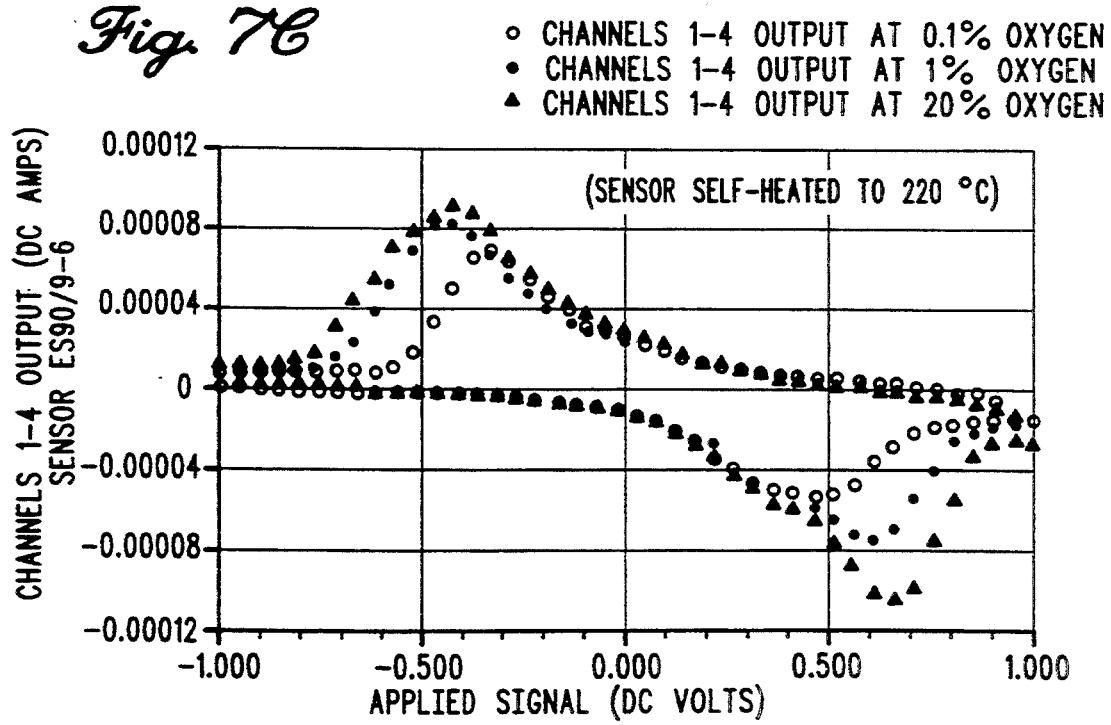

○ CHANNELS 1-4 OUTPUT AT 50s AFTER INJECTING VAPOR
● CHANNELS 1-4 OUTPUT AT 30s AFTER INJECTING VAPOR
▲ CHANNELS 1-4 DRY AIR PRIOR TO INJECTING VAPOR

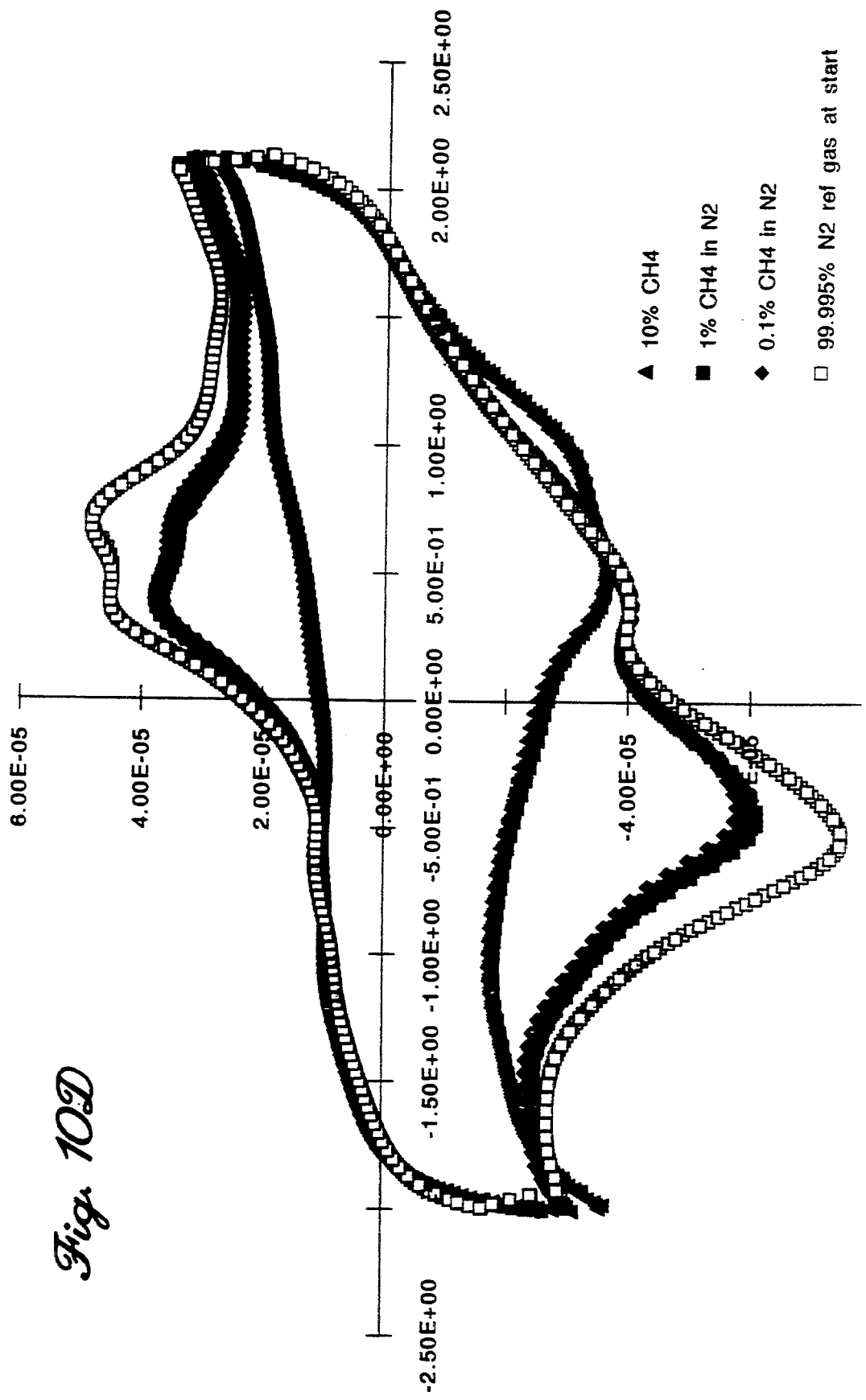

ELECTROCATALYTIC CERMET GAS DETECTOR/SENSOR

The United States Government has rights in this invention pursuant to Contract No. W-31-109-ENG-38 between the U.S. Department of Energy and The University of Chicago, Contractor for Argonne National Laboratory.

The present invention is concerned generally with a method and device for sensing gases and also for training gas sensors to recognize selected gases, including complex mixtures. More particularly, the invention is concerned with a method and device for sensing specific gases or mixtures thereof by providing catalytic action and/or varying a drive voltage being applied to the device to generate characteristic chemical signatures of a given gas or gas mixture. Such chemical signature data can be utilized to quantify gas species and amounts and train gas sensors to identify particular gas species.

Numerous industrial and consumer applications require use of sensitive, reliable gas detectors. These applications often involve use in a corrosive and/or high temperature environment. Such applications range over broad fields of use, such as for use in the automotive industry, the chemical processing field, the electrolytic processing industry, the electronics industry and in the area of general control of gaseous environments. Currently, sensors for such uses are of complex construction and frequently require devices having large and unwieldy structures. In addition, gas sensors often are dedicated to the measure of only a few gases and have little flexibility for measurement of a wide range of gases and of widely ranging concentrations.

It is therefore an object of the invention to provide an improved method and device for sensing gases.

It is another object of the invention to provide a novel method of detecting a variety of gases present in an environment.

It is also an object of the invention to provide an improved method and device for electrolytically detecting gases.

It is a further object of the invention to provide a novel method and device for detecting water vapor, gaseous organic chemicals and/or other gases alone or in combination.

It is yet another object of the invention to provide an improved method and device for performing highly sensitive detection of gases at lower temperatures.

It is still an additional object of the invention to provide a novel method and device for establishing a trained gas detection system for recognizing complex gas mixtures.

It is also another object of the invention to provide an improved method and device for dissociating gases to identify various gas species and quantify characteristic signal curves of particular gas species.

It is yet a further object of the invention to provide a novel layered device structure of a catalytic metal electrode with an intervening oxygen ion source and solid electrolyte enabling detection of gaseous species by catalytic activation.

It is still a further object of the invention to provide an improved system of analysis of gases by executing a neural network computer software program to characterize the gas.

These and other objects of the invention will become apparent from the following detailed description and the drawings described hereinbelow.

BRIEF DESCRIPTION OF THE DRAWINGS

FIG. 1AA shows a front plan view and FIG. 1AB shows a rear plan view of a gas sensor device constructed in accordance with the invention; FIG. 1B illustrates an exploded view of the gas sensor device of FIG. 1AA; FIG. 1C shows a cross section at the surface of the sensor device taken along 1C—1C in FIG. 1AA and FIG. 1D illustrates a cross sectional view of the entire sensor sandwich taken along 1D—1D in FIG. 1AA and for a device like FIG. 1AA but further including a Pt heating element layer;

FIG. 2 shows an exploded view of the individual layers making up another form of gas sensor device constructed in accordance with the invention;

FIG. 3A illustrates one form of gas sensor interconnected to a thermally insulating standoff interconnector and FIG. 3B shows a perspective view of a test clip for a self-heated gas sensor and FIG. 3C shows a top plan view of a test clip for a self-heated gas sensor device;

FIG. 4A shows a test chamber of a self heated gas sensor and FIG. 4B illustrates a tube furnace assembly for testing a gas sensor.

FIG. 7B shows the response of a second gas sensor; and FIG. 7C shows the response of a third gas sensor;

DETAILED DESCRIPTION OF PREFERRED EMBODIMENTS

Figure 4D:
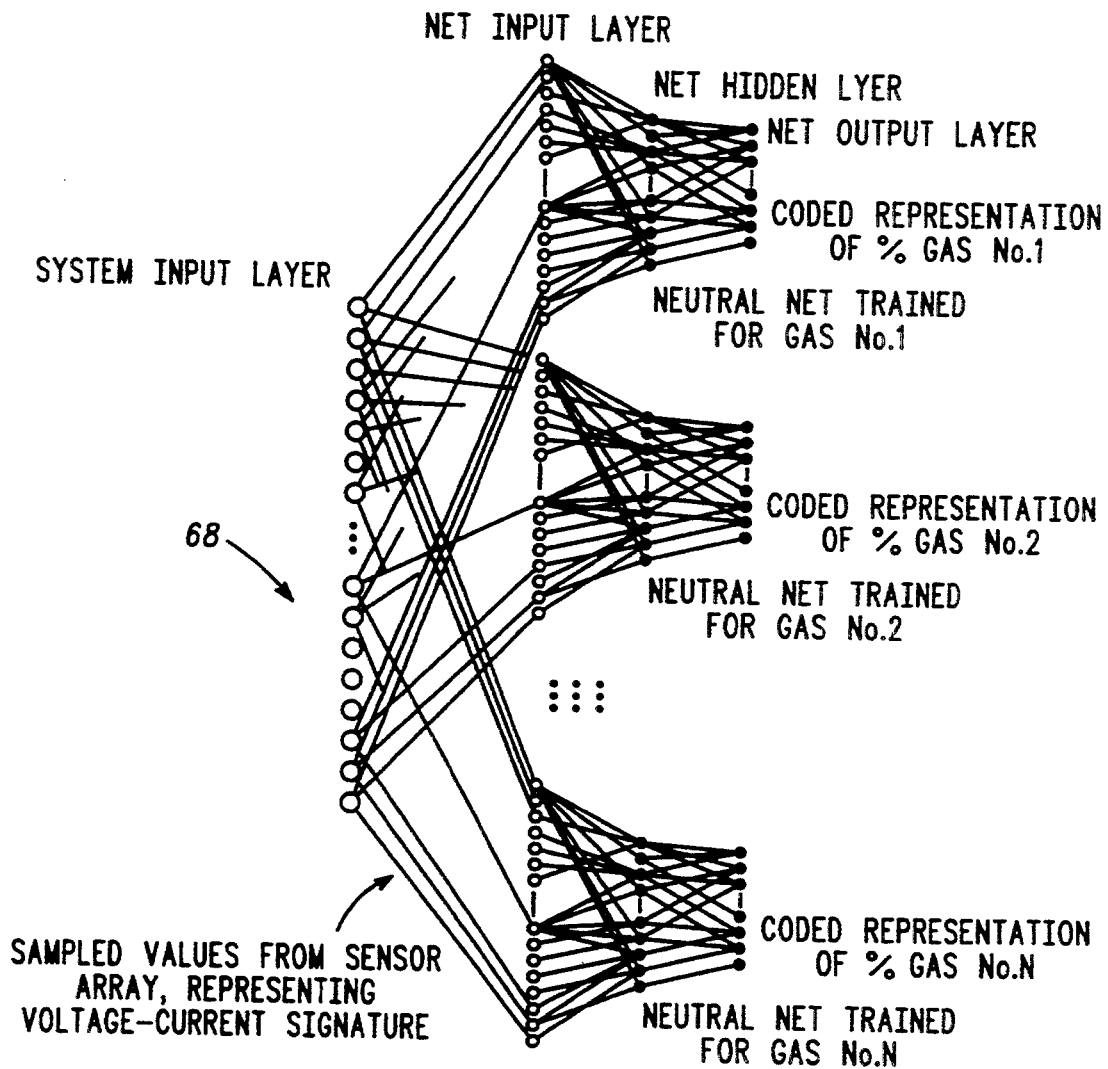
FIG. 4D shows a neural network structure diagram and FIG. 4E shows front views of virtual instruments in the data acquisition system of FIG. 4C.

A gas sensor device constructed in accordance with the invention is shown generally at 10 in FIGS. 1 and 2. Also see the schematic flow diagram in FIG. 11. As shown particularly in FIG. 1, the sensor device 10 includes a substrate 12. Deposited on the substrate 12 is a reference electrode 14 source of anions (hereinafter "reference electrode 14"), a lower reference electrode 16, a solid electrolyte 18 and an upper electrode 20. The gas sensor device 10 preferably also includes a coupled heating element 21 as shown in the embodiment of FIG. 1D. The substrate 12 can be any electrically nonconductive material which is chemically stable at temperatures of use, such as, for example, above 200° C. The substrate 12 also should be substantially impermeable to gas diffusion. Examples of such materials are ceramics like alma, spinel, mullire, forsterite and other such dielectrics.

The reference electrode 14 can be any one of a number of nonstoichiometric (e.g., anion deficient) metal oxides, metal sulfides, metal phosphides or combinations thereof which can act as a reversible source of anions and provide a reliable reference of partial pressure of the anion. Nonstoichiometric metal oxides, such as NiO, are particularly preferred for the reference electrode 14 since they provide a well buffered reference electrode of very low fixed oxygen activity in galvanic cells. Consequently, for example, the metal oxide combination provides an oxygen sink/source reservoir described by the equilibrium equation

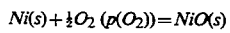

$$Ni(s) + \tfrac{1}{2}O_2\ (p(O_2)) = NiO(s)$$

where p(O₂) is the oxygen partial pressure. Equilibrium is achieved when pO₂ has penetrated the metal and oxide. Homogeneity of p(O₂) is maintained at the electrode/electrolyte interface by oxygen (anion) migration in the electrolyte and electron activity in the metal phase of the Ni/NiO system. The electron activity reaction is described by NiO(s)+2e=Ni(s)+O⁻ (electrolyte). Thus, in the nondriven mode of operation of the gas sensor device 10 (no variable voltage applied as described hereinafter in detail), the preferred metal oxide reference electrode 14 provides a stable reference of partial pressure for oxygen gas. This partial pressure data and voltage measured through the gas sensor device 10 via the Nernst equation can be used to determine an unknown oxygen partial pressure being monitored (or other anions, such as sulfur or phosphorous, or nitrogen or gas complexes containing such anions). In the general case, the partial oxygen (anion) pressure generated by a given metal oxide can be determined by calculating the equilibrium constant for the particular metal-metal oxide (anion) combination. In the driven mode of operating the gas sensor device 10 (applying a variable voltage as described hereinafter), the preferred metal oxide reference electrode 14 serves as an oxygen source which is driven to enhance oxidation reactions occurring on the face of the upper electrode 20. Suitable nonstoichiometric metal oxide systems for the reference electrode 14 are, for example, CdO, ZnO, CaO, CoO, CuO, FeO, MnO, VO, Ta₂O₂ CrO₃ and NiO.

In another form of the invention, the reference electrode 14 comprises a phosphide, sulfide (or other chalcogenide) system, such as, Ni/NiS, Zn/ZnS and other like combination systems (such as shown above for metal oxides) known to be operative as a reference electrode. Such materials can function to sense any type of gas, such as oxygen containing gases, not just sulfides or phosphide type gases.

The lower reference electrode 16 can also be used as a cathode as needed. This electrode 16 should be a good electrical conductor, such as, Pt, Cu, Ag and the like and most preferably is Pt.

The solid electrolyte 18 should function to permit the passage of the desired ions (such as, O, S, N, Cl, F and P) through the gas sensor device 10. The material for the solid electrolyte 18 can be selected from among a variety of ionically conductive solid electrolytes. In the case of oxygen ion conductors, examples of a preferred solid electrolyte can include, for example, yttria doped ZrO₂, CeO₂ and Bi₂O₃. The yttria doped ZrO₂ is most preferred due to its high oxygen ion conductivity, negligible electron conductivity, stability with respect to thermal decomposition and its well documented performance and characterization as an ionic conductor.

The upper electrode 20 is preferably a catalytically active material and also can act as the cathode of the gas sensor device 10. Consequently, the preferred upper electrode 20 is a catalytic metal, such as Pt, Ru, Rh, Os, Ir, Pd and for some uses, such as measurement of NO_x gas species Au can be used to lower the voltage level at which reactions of the NO_x species occurred. These catalytic materials optimize the promotion of oxidation of organic gas species contacting the electrode 20. Particularly in the voltage driven mode of operating the gas sensor device 10, the upper electrode 20 preferably acts to substantially promote gas oxidation. As will be shown in more detail hereinafter (including the figures), the electrical current dram between the lower reference electrode 16 and the upper electrode 20 at a particular applied voltage provides both quantitative and qualitative signature information, including data on redox potentials associated with particular gases or complex gas mixtures.

As explained in more detail in the Examples, during preparation of the gas sensor device 10 the firing of a Ni/NiO form of the reference electrode 14 causes diffusion of Ni/NiO for several microns into the upper surface of the substrate 12. Without limiting the scope of the invention, it is believed that the reaction of the Ni and NiO generates an equilibrium partial pressure of oxygen. This layer of the Ni/NiO reference electrode 14 is trapped between the aluminum oxide substrate 12 and a yttria stabilized zirconia form of the solid electrolyte 18 and forms a constant reference level of oxygen on one side of the yttria stabilized zirconia solid electrolyte 18. The yttria stabilized zirconia solid electrolyte 18 can then conduct oxygen ions and can build a voltage potential across its surfaces in response to different gas concentrations contacting the exposed surfaces of the gas sensor device 10.

The gas sensor device 10 is completed by the platinum upper electrode 20 which, along with the lower reference electrode 16 (preferably of platinum), senses the current flowing through the yttria stabilized zirconia solid electrolyte 18. In a preferred embodiment the platinum upper electrode 20 comprised a porous platinum material divided into a pad array such that if any pads are aligned with an electrically shorted pad of the yttria stabilized zirconia solid electrolyte 18, the pad column will not be connected, thus avoiding electrical signal shorting problems. All pads in columns which are not shorted can therefore be connected with platinum strips to become operative sensor elements. As shown in FIG. 2, a preferred embodiment uses strips of platinum 24 for the upper electrode 20 and lower reference electrode 16, respectively.

Figure 4E:
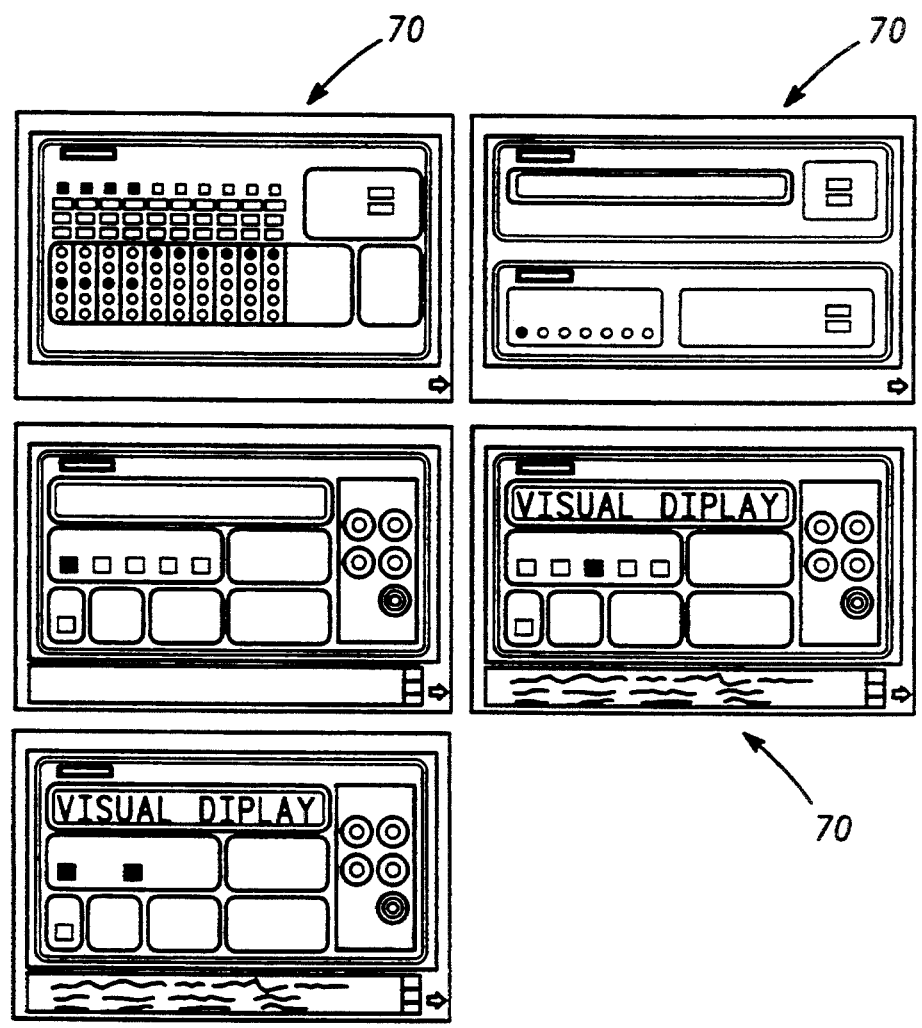
Figure 4C:
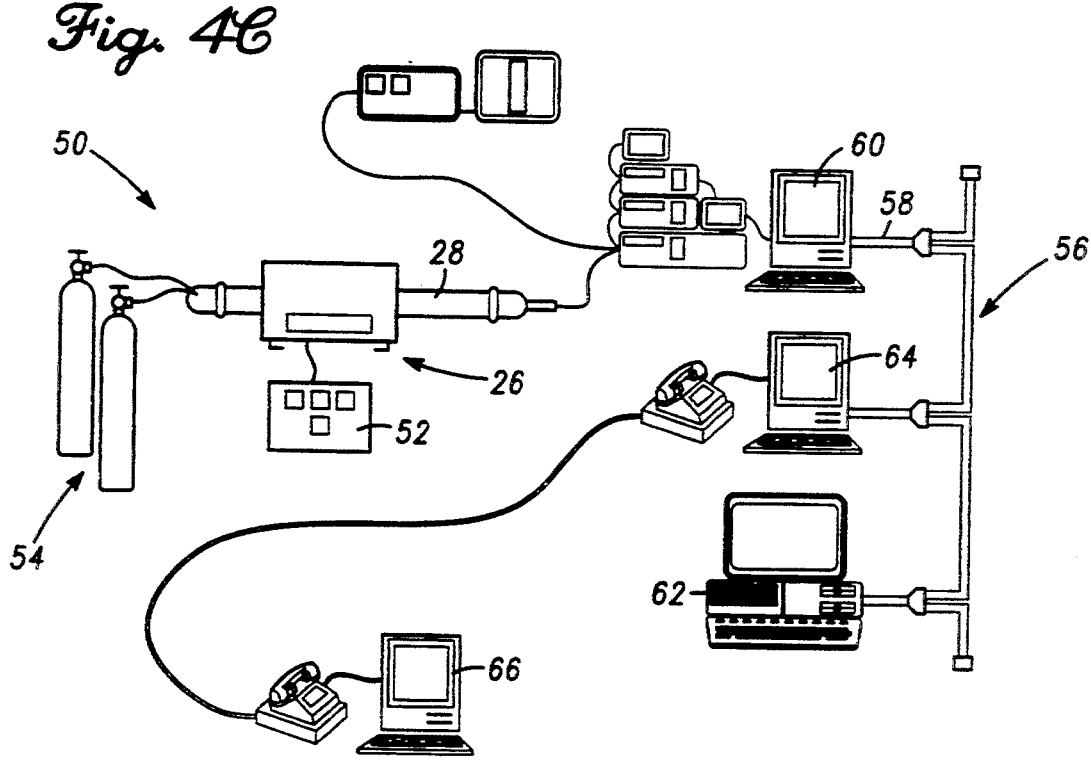
FIG. 4C shows a system for accumulating and analyzing data from a gas sensor.
Figure 5A:
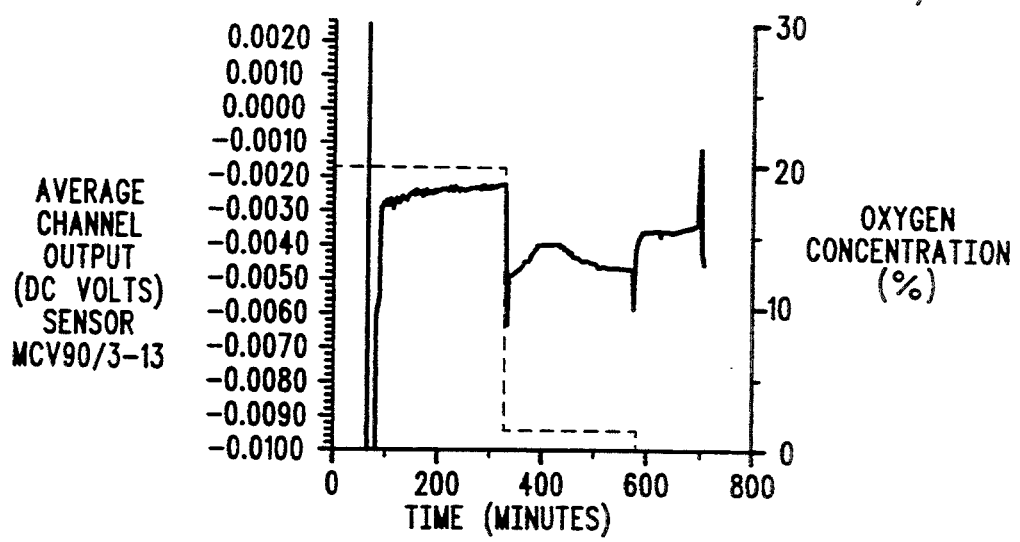
FIG. 5A illustrates the nondriven mode response of an externally heated sensor to changing oxygen gas concentrations.

In one form of the invention, heating of the gas sensor device 10 is accomplished by an external heat source, such as by a tube furnace 26 shown in FIG. 4C. The gas sensor device 10 can be disposed in a quartz tube assembly 28 which is coupled to the tube furnace 26, wherein the temperature was raised to about 500° C. during testing. These sets of tests were performed in a non-driven mode (no potential applied or varied). In the typical test routine three different oxygen concentrations were cycled across the gas sensor device 10, the quartz tube assembly 26 was evacuated, followed by flushing with the new oxygen gas concentration. As shown in FIG. 5A, three different oxygen concentrations were tested with the gas sensor device 18 showing good distinction between oxygen gas concentrations with some voltage spiking occurring when pressure changes took place.

Figure 5B:
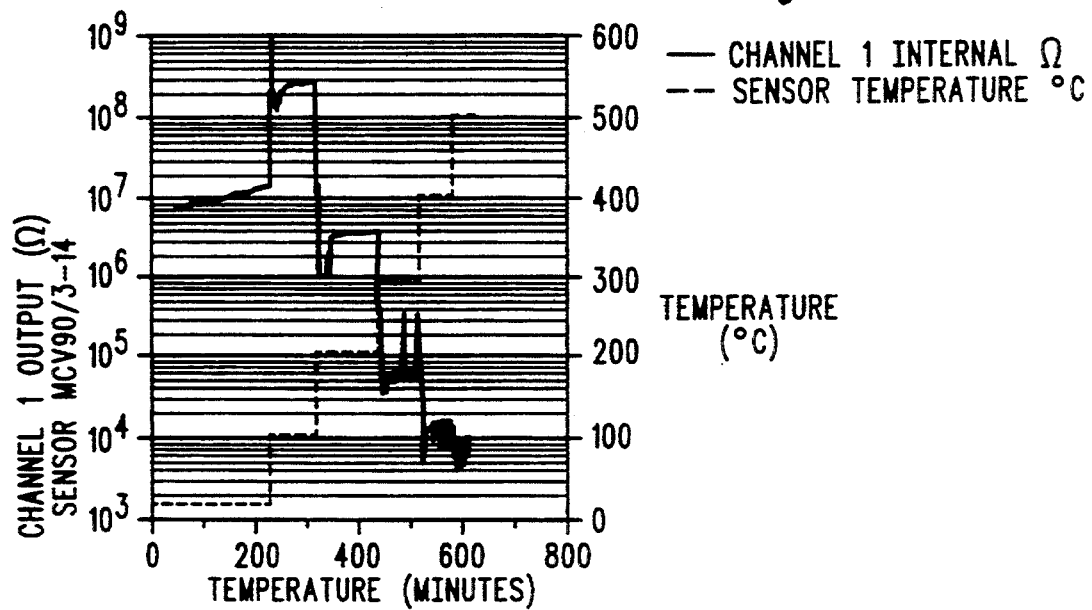
FIG. 5B shows a nondriven sensor internal resistance response to changing temperature of the sensor.
Figure 5C:
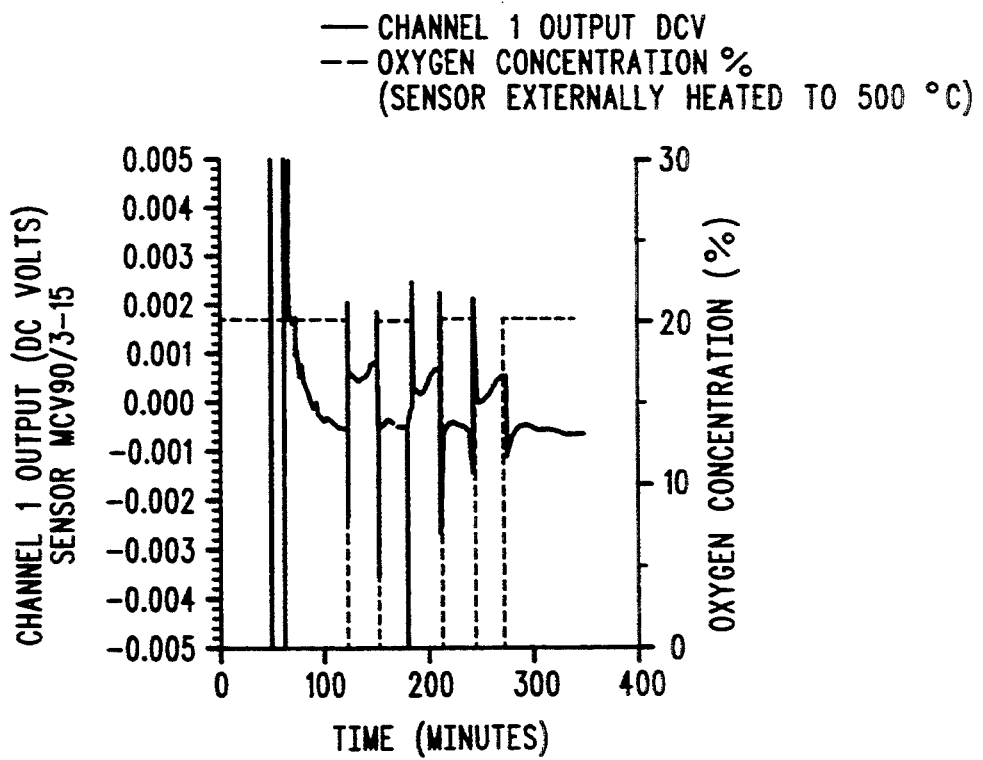
FIG. 5C shows the nondriven mode response of the gas sensor to cycling gas concentrations.
Figure 5D:
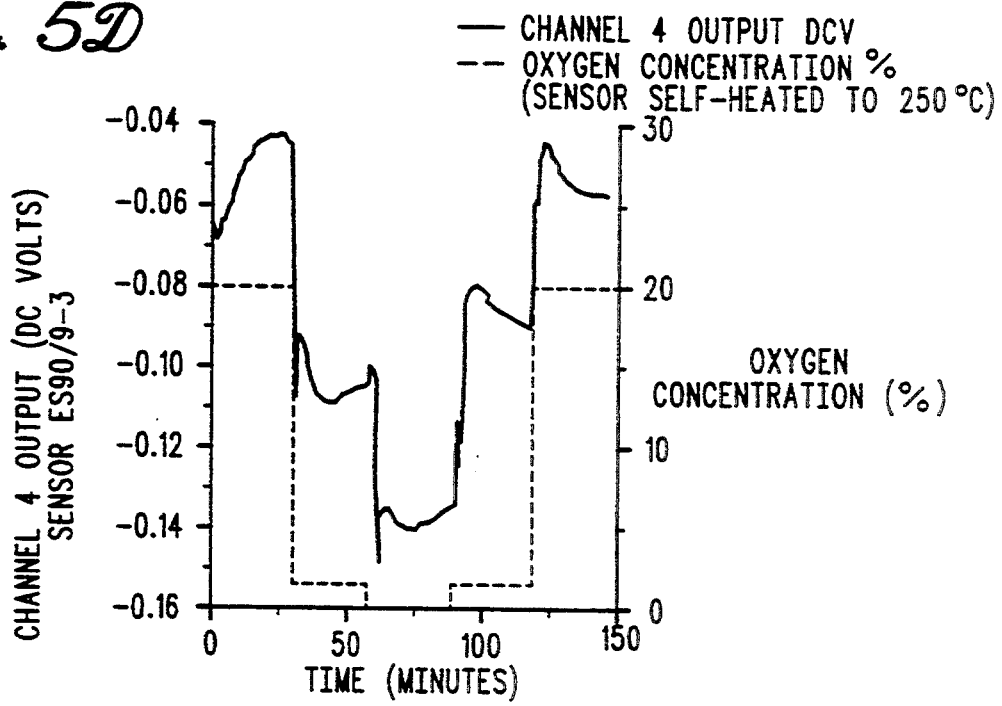
FIG. 5D shows the nondriven mode response of a self-heated nondriven first sensor to changing oxygen concentrations.
Figure 5E:
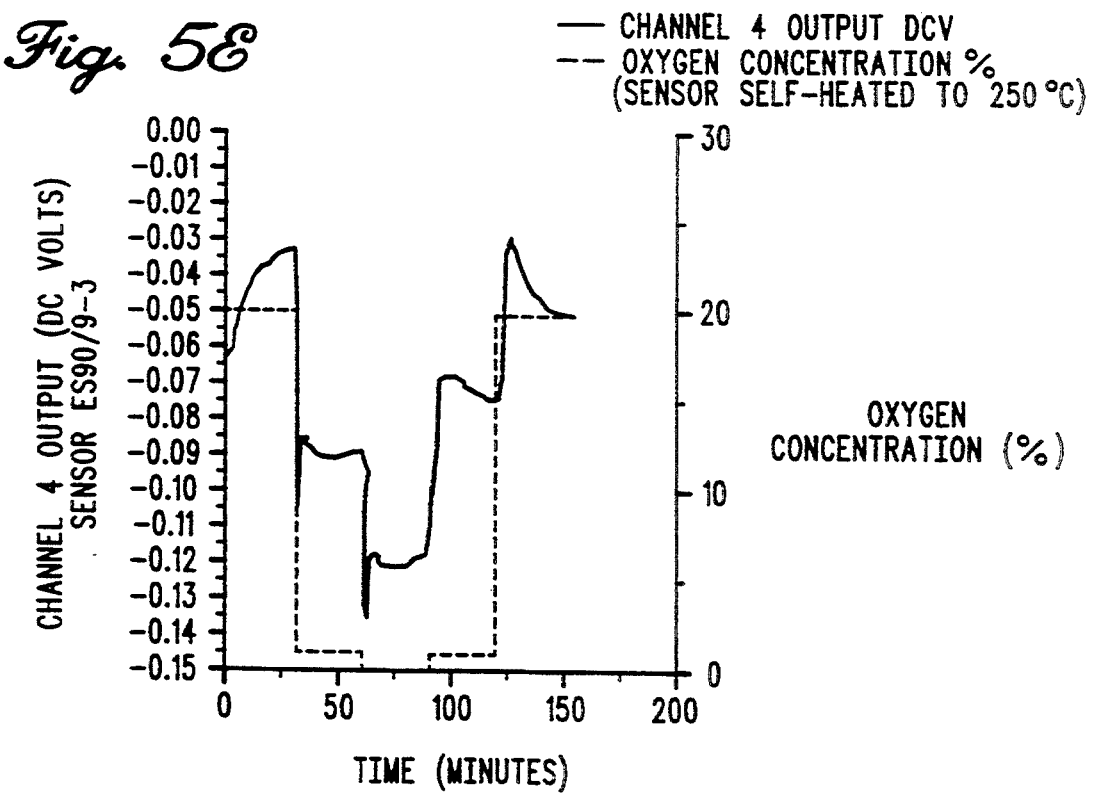
FIG. 5E illustrates the response of a self-heated, nondriven second sensor to changing oxygen concentration.
Figure 5F:
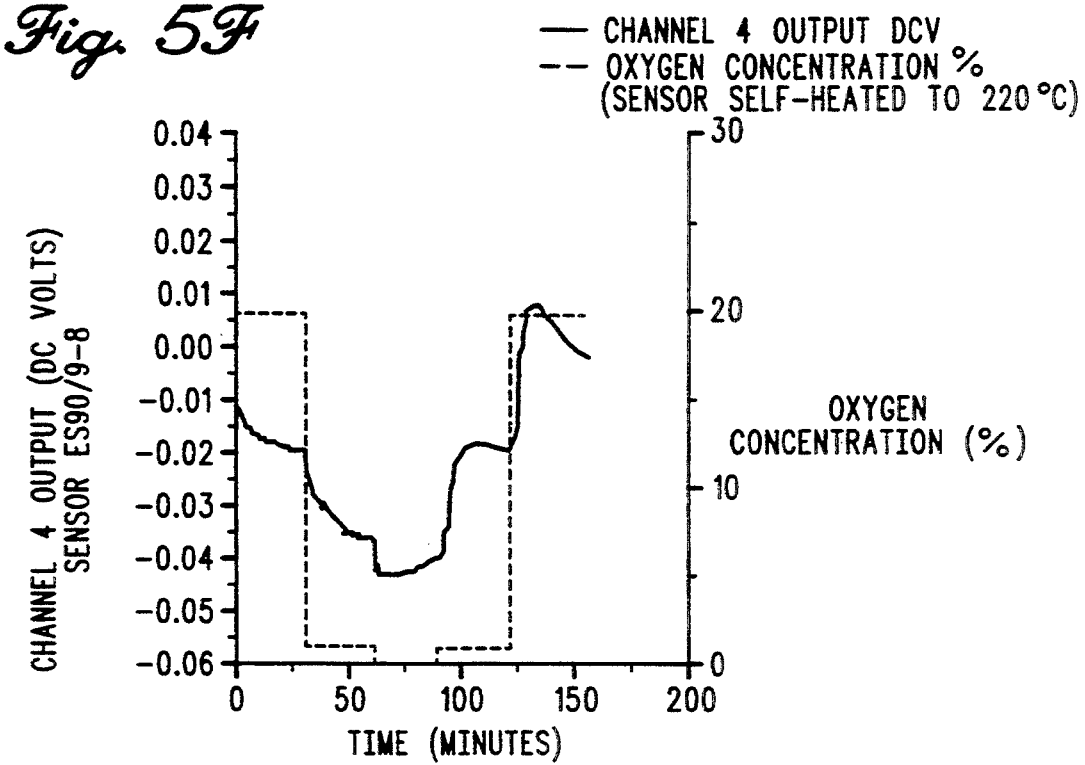
FIG. 5F shows the response of a self-heated nondriven third sensor to changing oxygen concentration and FIG. 5G shows the response of a self-heated, nondriven fourth sensor to changing oxygen concentration.
Figure 5G:
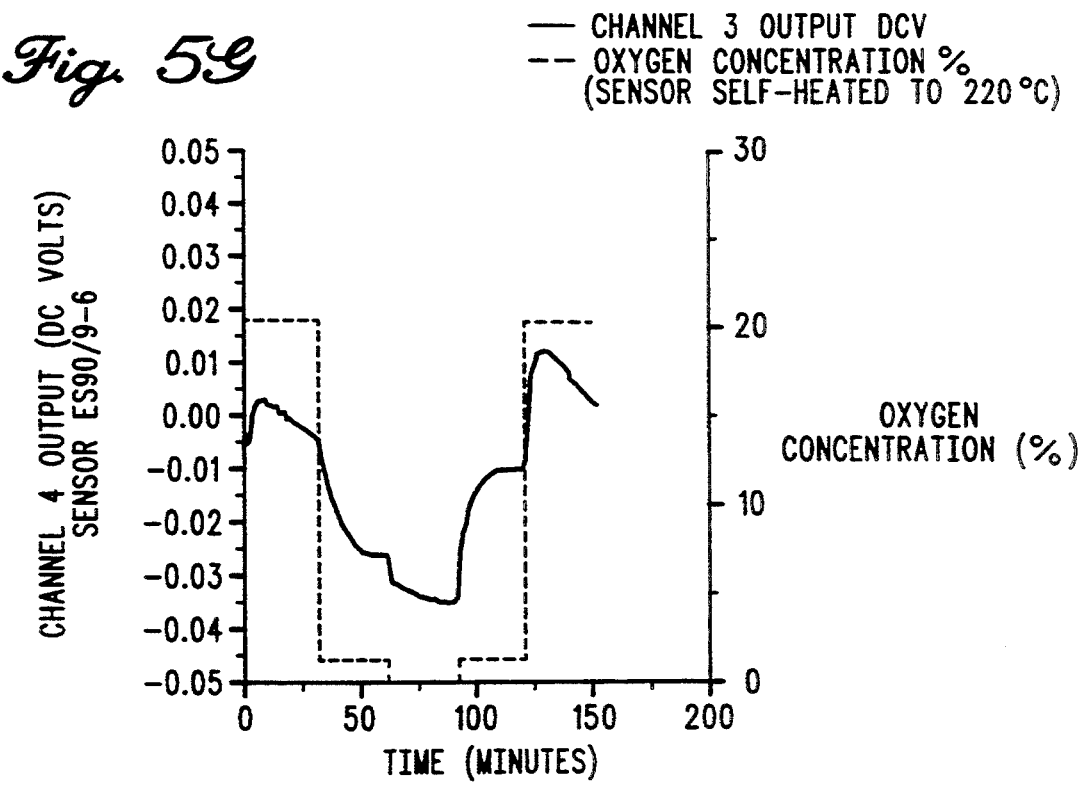

It was useful to characterize the gas sensor device 10 in the quartz tube assembly 28 by testing the following: (a) its internal resistance against temperature, (b) its repeatability of response to cycled gas inputs, and (c) its response to stepped gas concentration changes. As shown in FIG. 5B under nondriven voltage operation, the resistance versus temperature plot shows that a first clean plateau in resistance occurred at about 200° C. This preferred testing temperature range (above 200° C.) was used in most of the self heating tests of the gas sensor device 10. As further shown in FIG. 5C, the gas cycling tests showed good repeatability for the gas sensor device 10.

In the preferred form of the invention, the gas sensor device 10 is self-heated to establish a controlled temperature for the analysis conditions which enables achievement of highly reliable test conditions. As shown in FIGS. 1D and 2, the Pt heating element layer 21 provides this capability of self-heating of the gas sensor device 10. The layer 21 has a resistance of about one hundred ohms and can be readily used with existing Pt resistance temperature detector thermometers which employ Pt resistive elements to sense temperature. Therefore, by designing the resistance of the layer 21 to be the same value, the layer 21 can itself be used to measure the temperature of the gas sensor device 10. For calibration purposes, the measured temperatures were checked against a low mass thermocouple.

In one preferred form of testing the invention, the gas sensor device 10 was coupled to an insulated thermal stand-off 32 which included a plurality of Pt strips 34 on a second insulator substrate 36 (see FIG. 3A). Platinum wires 38 were coupled between the Pt strips 34 and the gas sensor device 10. The stand-off 32 was then inserted into a plastic edge connector (not shown) with test equipment leads (not shown) attached to the edge connector. This geometry enabled the gas sensor device 10 to operate at high temperatures with only the platinum wires 38 to transfer heat to the stand-off 32. In other embodiments, gold wires and gold strips in the stand-off 32 can be used.

In a more preferred method of testing the invention, a test clip 40 was used to make electrical connections to the gas sensor device 10 undergoing gas testing. As shown in FIGS. 3B and 3C, a nylon form of IC test clip 40 can be used to hold the gas sensor device 10. Since the nylon shell of the test clip 40 is spaced apart from the contacts with the gas sensor device 10, the test clip 40 is unaffected by the elevated operating temperature used for the self-heating tests. Accurate temperature calibrations could also be made by placing a small, low mass thermocouple under one of the fingers of the test clip 40, thereby being held tightly against the gas sensor device 10.

A testing program for self-heating characterization of the gas sensor device 10 included preparation of a batch of six of the devices 10 prepared in the same manner (see Examples I and II). The self-heated gas sensor devices 10 were heated and exposed to different gases and particularly to oxygen in a nitrogen gas base. The gas concentrations were changed at different rates, the duration of maintaining a gas concentration was changed, and the voltage produced by the gas sensor device 10 was measured. The test matrix for the self-heated tests of the gas sensor device 10 is shown in Table I below:

TABLE I

| SENSOR TESTED | SENSOR TEST PARAMETERS | | |
|---|---|---|---|
| | GAS CYCLING SPEED | SENSOR TEMPERATURE | OXYGEN CONCENTRATION |
| ES90/9-1 | | | |
| Test 1 | 60 min/gas | 26° C. | 19% |
| Test 2 | 60 min/gas | 26° C. | 1% |
| Test 3 | 60 min/gas | 26° C. | 0.10% |
| Test 4 | 60 min/gas | 100° C. | 19% |
| Test 5 | 60 min/gas | 100° C. | 1% |
| Test 6 | 60 min/gas | 100° C. | 0.10% |
| Test 7 | 60 min/gas | 220° C. | 19% |
| Test 8 | 60 min/gas | 220° C. | 1% |
| Test 9 | 60 min/gas | 220° C. | 0.10% |
| Test 10 | 30 min/gas | 26° C. | 19% |
| Test 11 | 30 min/gas | 26° C. | 19% |
| Test 12 | 30 min/gas | 26° C. | 0.10% |
| Test 13 | 30 min/gas | 100° C. | 19% |
| Test 14 | 30 min/gas | 100° C. | 1% |
| Test 15 | 30 min/gas | 100° C. | 0.10% |
| Test 16 | 30 min/gas | 220° C. | 19% |
| Test 17 | 30 min/gas | 220° C. | 1% |
| Test 18 | 30 min/gas | 220° C. | 0.10% |
| Test 19 | 15 min/gas | 26° C. | 19% |
| Test 20 | 15 min/gas | 26° C. | 1% |
| Test 21 | 15 min/gas | 26° C. | 0.10% |
| Test 22 | 15 min/gas | 100° C. | 19% |
| Test 23 | 15 min/gas | 100° C. | 1% |
| Test 24 | 15 min/gas | 100° C. | 0.10% |
| Test 25 | 15 min/gas | 220° C. | 19% |
| Test 26 | 15 min/gas | 220° C. | 1% |
| Test 27 | 15 min/gas | 220° C. | 0.10% |

THIS BATTERY OF TESTS WAS REPEATED FOR EACH

TABLE I-continued

SENSOR TEST PARAMETERS

| SENSOR TESTED | GAS CYCLING SPEED | SENSOR TEMPERATURE | OXYGEN CONCENTRATION |
|---|---|---|---|
| OF THE SIX SENSORS IN THIS BATCH | | | |

The resulting measured voltages are shown in FIGS. 5D–5G.

In the most preferred embodiment, the gas sensor device 10 was used in a driven mode to generate a characteristic signal for the gas being detected. The driven mode masked any differences between individual ones of the gas sensor devices 10 by virtue of using a driving voltage larger than the voltage generated by the gas sensor device 10. In the driven tests, a voltage potential was applied to the lower reference electrode 16 and upper electrode 20, respectively, from an external source (not shown) which forced migration of oxygen ions through the yttria stabilized zirconia solid electrolyte 18. This ion migration was measured as an electrical current and processed as described hereinafter by system 50 (see FIG. 4C).

Figure 6:
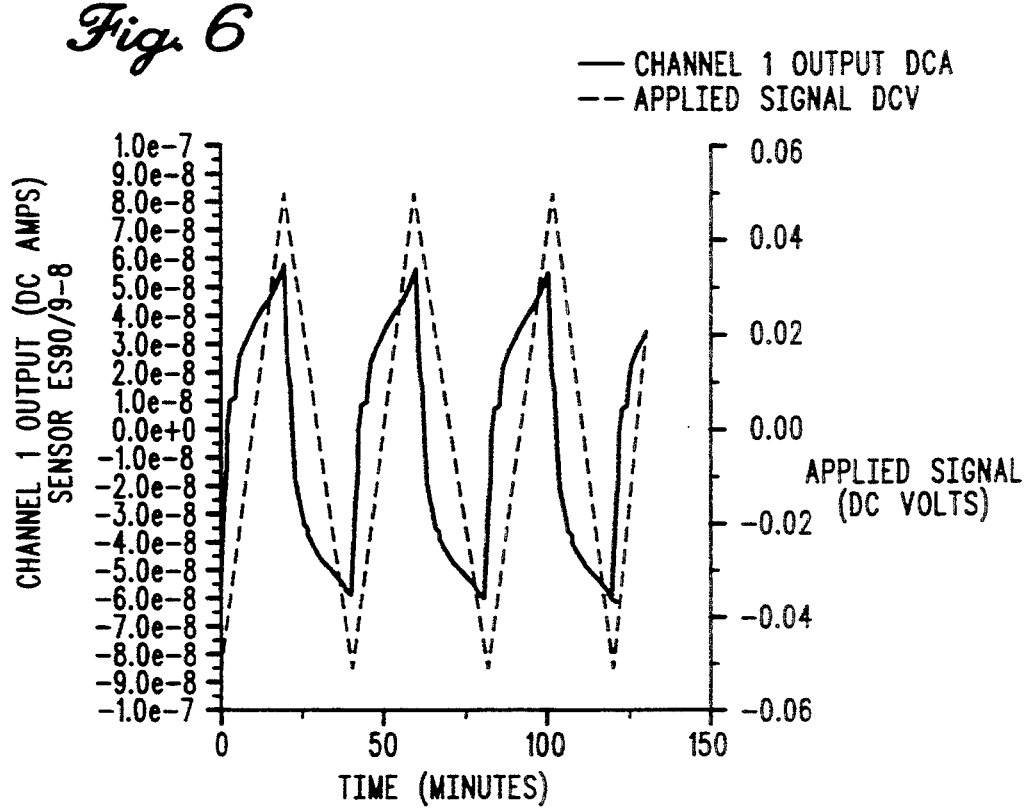
FIG. 6 illustrates the response of a self-heated, driven gas sensor to applied voltage for fixed oxygen concentration.

The driven test method of operation involved generating a ramping voltage of the same magnitude as that developed by the gas sensor device 10 alone. This test was done to avoid damaging the film by pumping too much oxygen into the gas sensor device 10 which could cause blistering of the layers comprising the sensor 10. After observing that the gas sensor device 10 could withstand larger voltages, the supply voltage was increased to the level needed to begin to disassociate gases on the upper sensing platinum electrode 20 (see FIG. 6 for shape of the applied DC voltage). One of the test signals used was a ±1 VDC triangular wave with a period of fifty seconds.

Figure 11:
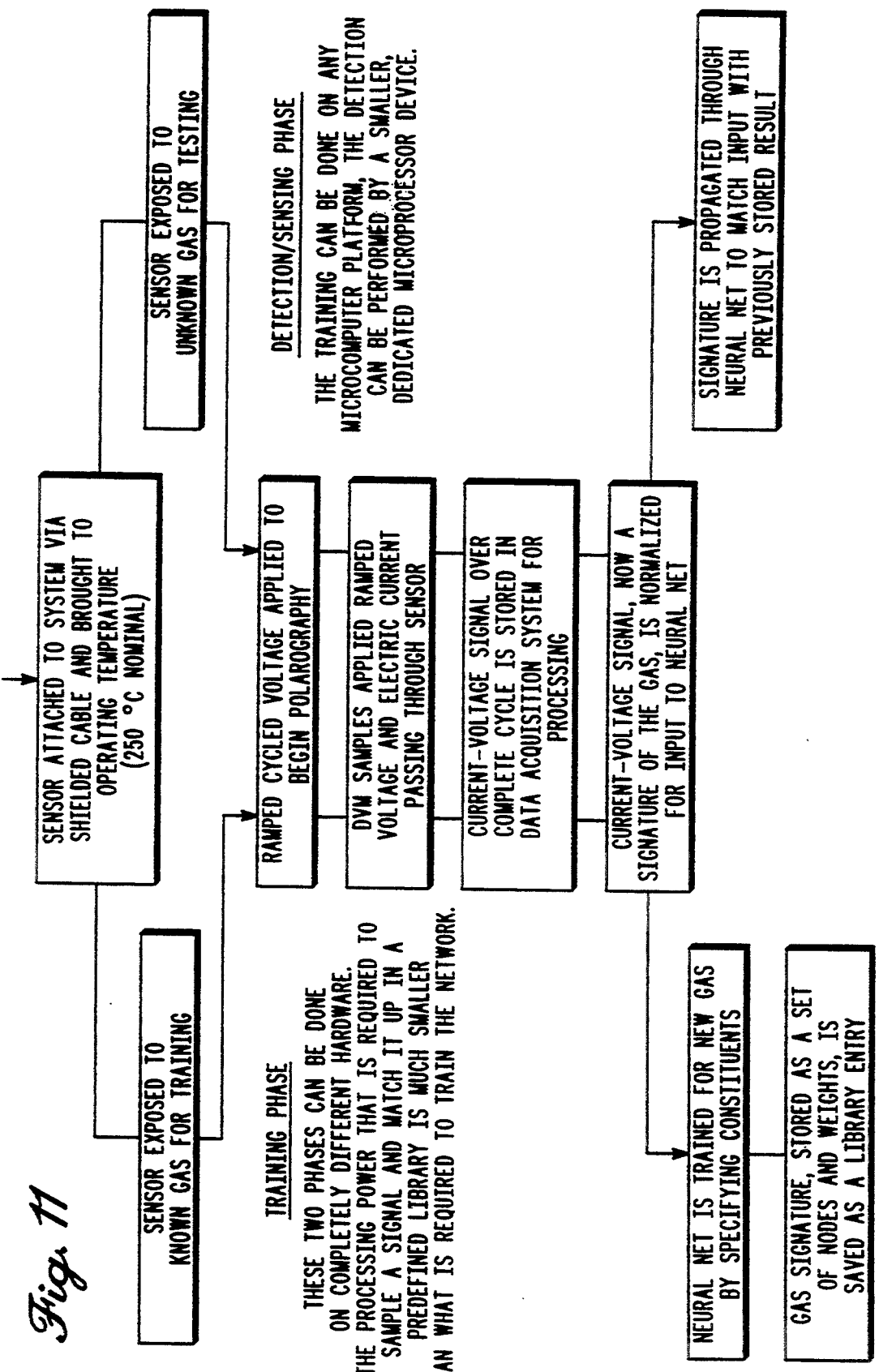
FIG. 11 is a schematic flow diagram of operation of the gas sensor device in several modes, including gas detection and sensor training.

The system 50 as shown in FIG. 4C includes the gas sensor device 10. (not shown) disposed within the quartz robe assembly 28 which is positioned within the robe furnace 26 having controller 52. The test gases used were contained in tank system 54 and input into the robe furnace 26 for characterization by the gas sensor device 10. A data acquisition system 56 samples the electronic signal (DC current) output from the gas sensor device 10 at a rate of 2 Hz. The data acquisition system 56 can include a local CPU 58 (such as a dedicated microprocessor or a personal computer 60), a remote CPU 62, a large computer system 64 or a modem connected PC station 66. The accumulated data is further processed using the neural network 68 functionally shown in FIG. 4D which includes virtual instruments 70 shown in FIG. 4E. The computer system (such as the large computer system 64 or the PC station 66) can execute a computer program including a virtual instrument code (see Appendix). The computer program includes subroutines to accumulate and analyze the incoming data and output a signal for review and/or plotting (see example in FIG. 11). As shown in FIG. 4E, the virtual instruments 70 are used to mimic and control the various parts of the electronic equipment to allow easier operation and debugging. The computer program is written in modules which emulate digital voltmeters, resistance meters and RLC bridges. Embedded in the computer program is a neural net module which is treated as a function called up by the appropriate computer system, and the neural net module operates on the data which is characteristic of a sampled representation of the gas signature. In the case of accumulating a gas signature library, a back propagation net is constructed by the neural net module. During the training phase of the neural net module, the sampled gas data is compared to a known, desired output signal. The internal weights representing the sampled gas are altered until a particular error constraint is met. A separate neural net module can be trained for each gas mixture of interest. See the schematic flow diagram in FIG. 11 showing operation of one form of sensor training mode. The training can include samples for changing concentration of the same gas mixture, as well as corrections for humidity and temperature. The trained neural net module will then accept an unknown gas concentration along with measurements for correcting for temperature and humidity to yield a value for the concentration of that gas in the sampled mixture. The computer program can thus perform pattern recognition analysis when it is desirable to train the gas sensor device 10 to recognize complex gas mixtures or various particular gas mixtures, such as innocuous fumes of burnt paper (see FIG. 12A) versus harmful burning plastic or burning electronic circuit boards (see FIG. 12B).

In another form of the invention, the neural net module enables processing of data characteristic of a completely unknown gas mixture, analyzing the data by the neural net module and patterns are detected without training. In this mode of operation, the system 50 can be used for analytical purposes as opposed to threshold-/control system usage.

Figure 7A:
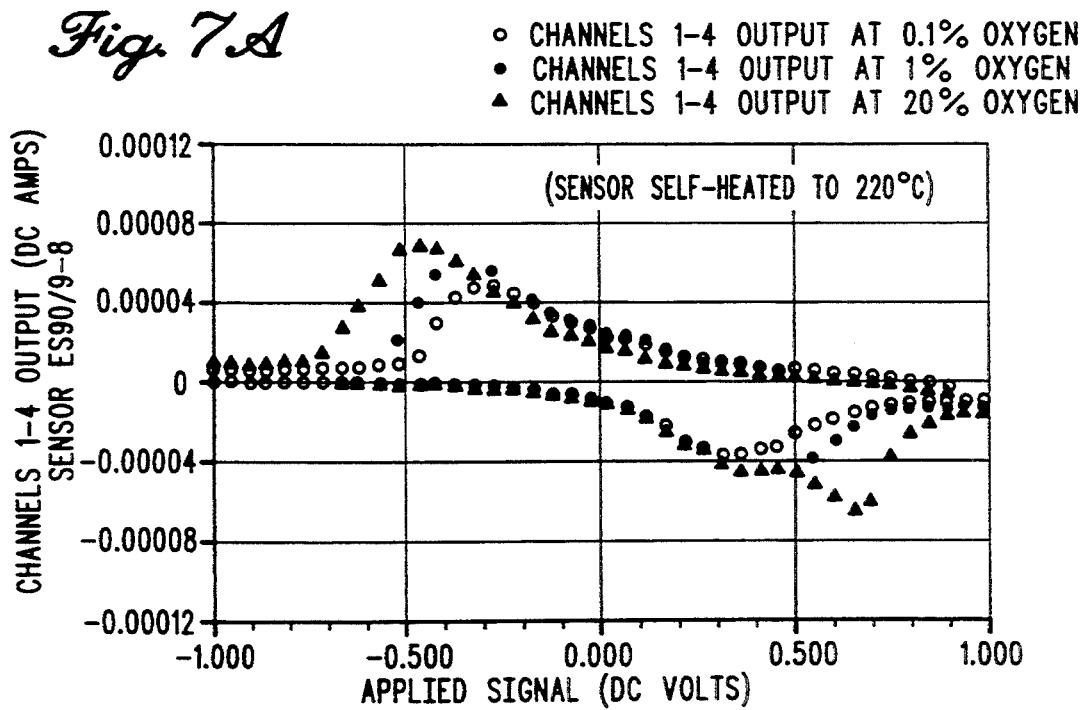
FIG. 7A shows the response of a first self-heated, gas sensor to applied voltage variation in the presence of (3) different oxygen concentrations.

The system 50 can therefore provide a plot of measured current vs applied voltage with one-hundred data points, which was sufficient to define the shape of the sensors' response to the gas atmosphere. Four of the five sensing strips of platinum 24 (see FIG. 2) on the gas sensor device 10 were measured individually as channels 1,2,3, and 4. This allowed the sensor construction to be studied and allowed for the elimination of any sensing element that showed too great a variance from the other elements. If the sensor channels showed no variance problems, then the channels were shorted together and the gas sensor device 10 was measured as a single channel (see FIGS. 7A–7C). The gas sensor device 10 was then exposed to oxygen concentrations of 20%, 1%, and 0.1% (also see Example III). The tests began by heating the gas sensor device 10 to an operating temperature of about 220° C. and allowing the temperature to equilibrate. Different induction times were tested and a sixty minute (minimum) warm-up time was found to give the most uniform response to gas changes. In this warm-up period the sensor device 10 was continually driven by the ±VDC-fifty second period ramped input. The tests then began by flushing the tube furnace 26 (or other chamber) which contains the gas sensor device 10 for five minutes at 5 L/minute with the gas of interest followed by flushing for five minutes at 0.1 L/minute. With the new gas atmosphere in place, data were collected for one complete period starting at the negative end of the input ramp (−1 VDC). The one complete period included one or more voltage scans, biasing the platinum upper electrode 20 positive then negative. The graphs for a typical test consisted of three curves, one for each of the three standard test gases used. As shown in FIGS. 7A–7C, the curves were superimposed to compare the current-voltage envelopes. The higher concentrations of oxygen exposed to the platinum upper electrode 20 produced larger current-voltage envelopes. The higher concentrations of oxygen exposed to the platinum upper electrode 20 also produced current shifts in the gas sensor device 10 that earlier showed the most distinct non-driven responses.

Figure 8A:
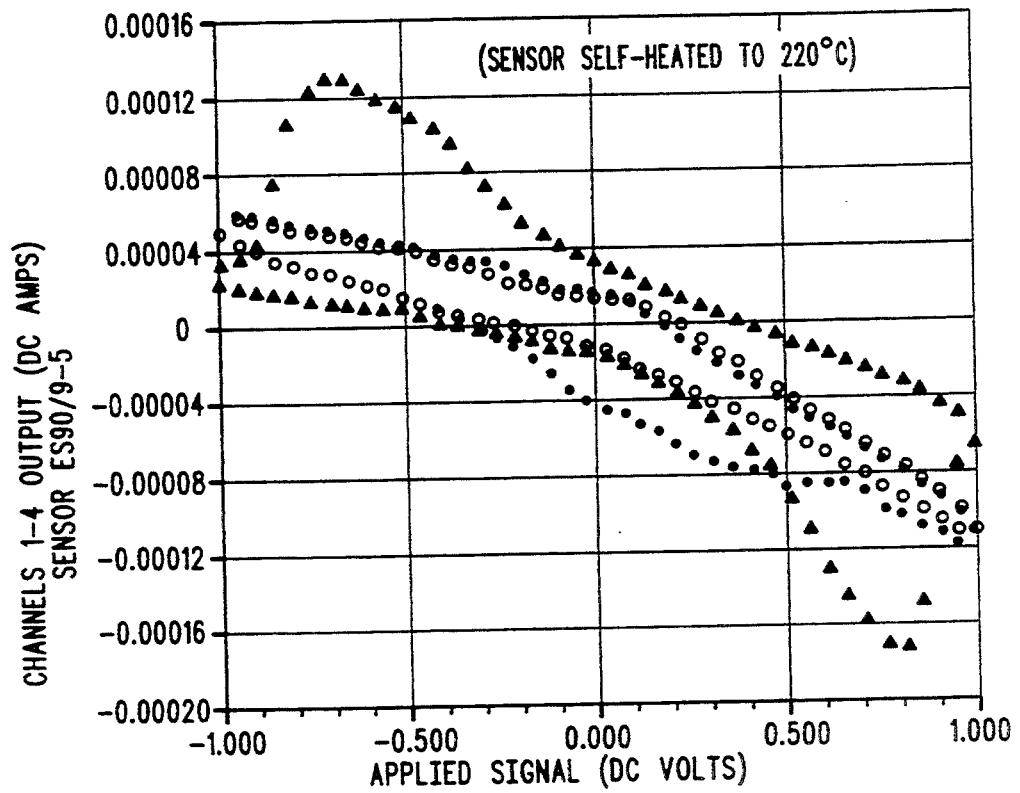
FIG. 8A shows the response of a self-heated, voltage driven gas sensor to toluene vapors.
Figure 8B:
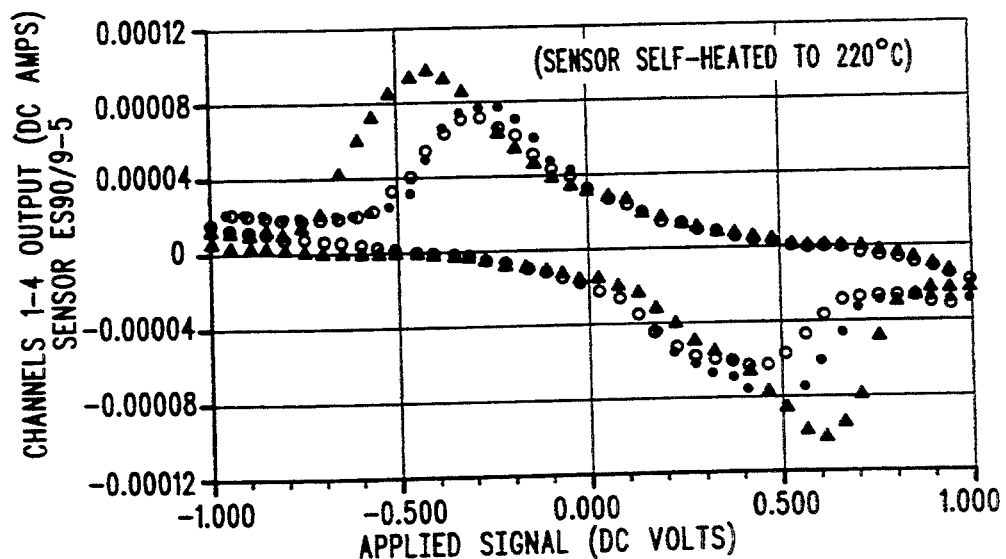
FIG. 8B shows the response of a self-heated, voltage driven gas sensor to Xylene vapors.
Figure 8C:
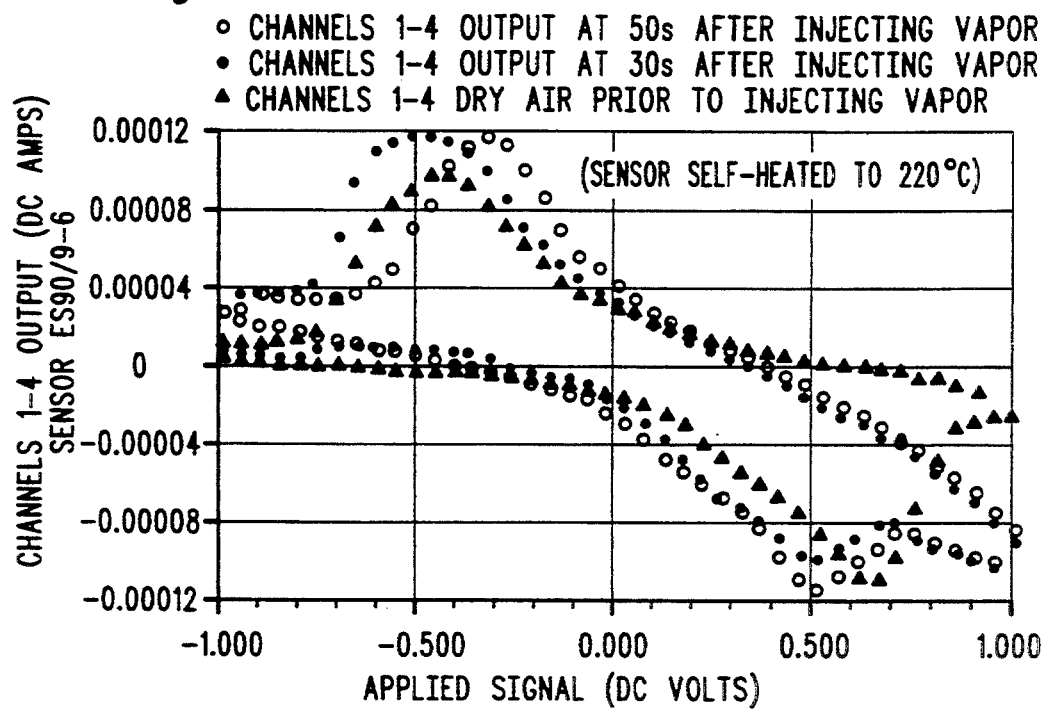
FIG. 8C shows the response of a self heated voltage driven gas sensor to 1,2 dichloroethane vapors.

Testing of the response of the gas sensor device 10 to organic vapors illustrates the ability to use the device 10 as a catalytic type of sensor. The same gas sensor device 10 and test equipment were used in these tests as in the earlier oxygen driven-response tests. To begin these tests, dry analyzed air from a gas cylinder was used as a 'carrier' gas much like helium and hydrogen carrier gases in gas chromatographs. Sample organic vapors were produced by drawing ten mL of liquid into a sixty mL glass syringe (not shown). The liquid was ejected and sixty mL of ambient air was drawn into the syringe and the syringe was capped. The gas sensor device 10 was mounted and brought up to an operating temperature of 200° C. The gas sensor device 10 was held at that temperature while a carrier stream of dry air flowed at 0.1 L/min for sixty minutes. The chamber ambient temperature was approximately 52° C. The gas sensor device 10 was then sampled by the data acquisition system 50 by applying voltage-driven conditions of three successive ±1 VDC-50 s triangle input periods. The first period represented the sensor response to the dry air. At the start of the second period, the sample organic vapors were injected over a ten second span from the glass fifty mL syringe. The second and third periods represent the response to mixing and mixed organic gases. The initial tests (see FIGS. 8A–8C) show sensor response to several organic solvents, including toluene, xylene, and 1,2 dichloroethane. All tested vapors showed marked changes in the sensors' current-voltage envelope, thereby demonstrating the capability of identifying particular gas species. FIG. 11 illustrates schematically the operation of the gas sensor device 10 in a gas detection mode as well as a sensor training mode.

The following nonlimiting examples set forth methods of preparation and further testing of gas samples illustrative of several embodiments of the invention.

EXAMPLE I

Preparation of thick film sensor inks, substrates and screen printing was carried out by the following procedure:

Heraeus Cermally VS2584 electronic vehicles were used to carry the pigments. The reference electrode ink (ES/RE-7) was prepared with spray-dried nickel oxide pigment obtained from Johnson Matthey Materials Technology (physical composition 70% solids and 30% vehicle). Solid Electrolyte ink (ES/SE-1) was prepared with spray-dried yttria stabilized zirconia from Toyosoda (physical composition 40% solids and 60% vehicle). Spray-dried inks were pulverized and combined with the vehicle with a ground-glass fiat-bottomed pestle and glass plate. The platinum electrode ink (ES/C-9) was prepared with a smooth Pt conductor paste from Heraeus Cermalloy (physical make up 68% Pt paste and 32% vehicle). This ink does not need to be pulverized and is easily blended with the vehicle by hand without the use of the mortar and pestle.

The substrates used were Coors TM ceramic aluminum oxide ($Al_2O_3$) substrates that measured 12 mm×13 mm×0.625 mm and were used for the sensors. They were factory-fired between plates for uniform surface roughness. Prior to use they were cleaned in an ultrasonic bath and kept covered to prevent contamination. The substrates were labeled on one side with a cobalt nitrate ink that, when heated on a hot plate, turned a bright permanent blue that did not fade at high temperatures and remained legible.

Screen printing was a Presto TM Model A9M0303 industrial screen printer with an adjustable mounting table and built-in video display camera was used for this work. This printer could accurately place films within ±125 μm. The substrates were mounted 2 mm below the screens. The films screened were 10–20 μm thick and fired to about half that thickness.

The printer screens consisted of a stainless-steel woven mesh stretched tightly over a frame with a stencil of light-sensitive photographic emulsion adhered to the center. The screen was mounted on an automatic press. A squeegee pressed ink through the mesh onto a mounted substrate at a constant pressure and rate. The screens used for this work were mounted on a 12 cm×12 cm aluminum frame. The platinum ink patterns were made on a 300 mesh 45° strung screen, while the nickel and yttria-stabilized zirconia patterns were made on a 240 mesh 45° strung screen. The tension of the screens on the frame was measured at a 1 mm deflection with a 500 g load.

EXAMPLE II

Figure 9A:
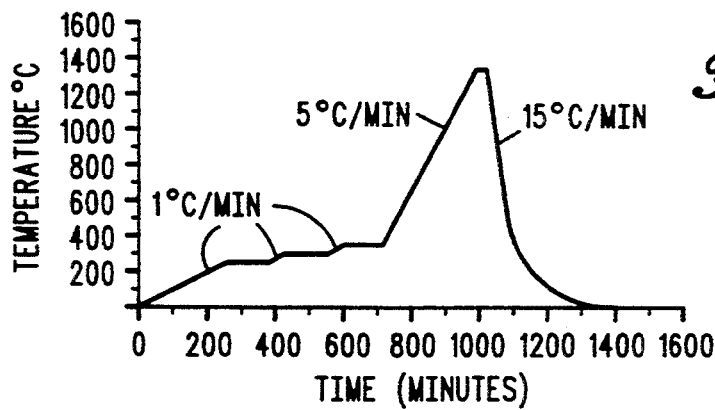
FIG. 9A illustrates a furnace firing schedule for preparing a screened thick film gas sensor device and FIG. 9B shows another furnace firing schedule for a gas sensor device.
Figure 9B:
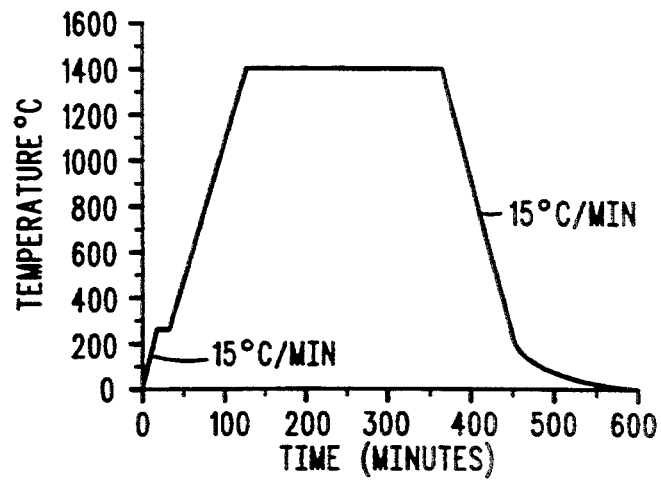

The gas sensor devices were prepared by forming the layer pattern in accordance with Example I and then firing in a Lindberg TM Super Kanthal furnace controlled by a Eurothenn TM programmable controller. The firing schedules were implemented as shown in FIG. 9A and 9B. The slow ramping up to 350° C. was used to keep the rate of out-gassing of the organic vehicle to a minimum. Quickly heating the organic vehicle to sintering temperatures caused the solvent to boil and damaged the film surface. All organic materials burned off at approximately 250° C. Increasing the sensor temperature to 1350° C. sintered the Ni/NiO and YSZ components, and the additional firing schedule to 1400° C. for four hours ensured that the migration of the NiO into the substrate was complete.

EXAMPLE III

Figure 10A:
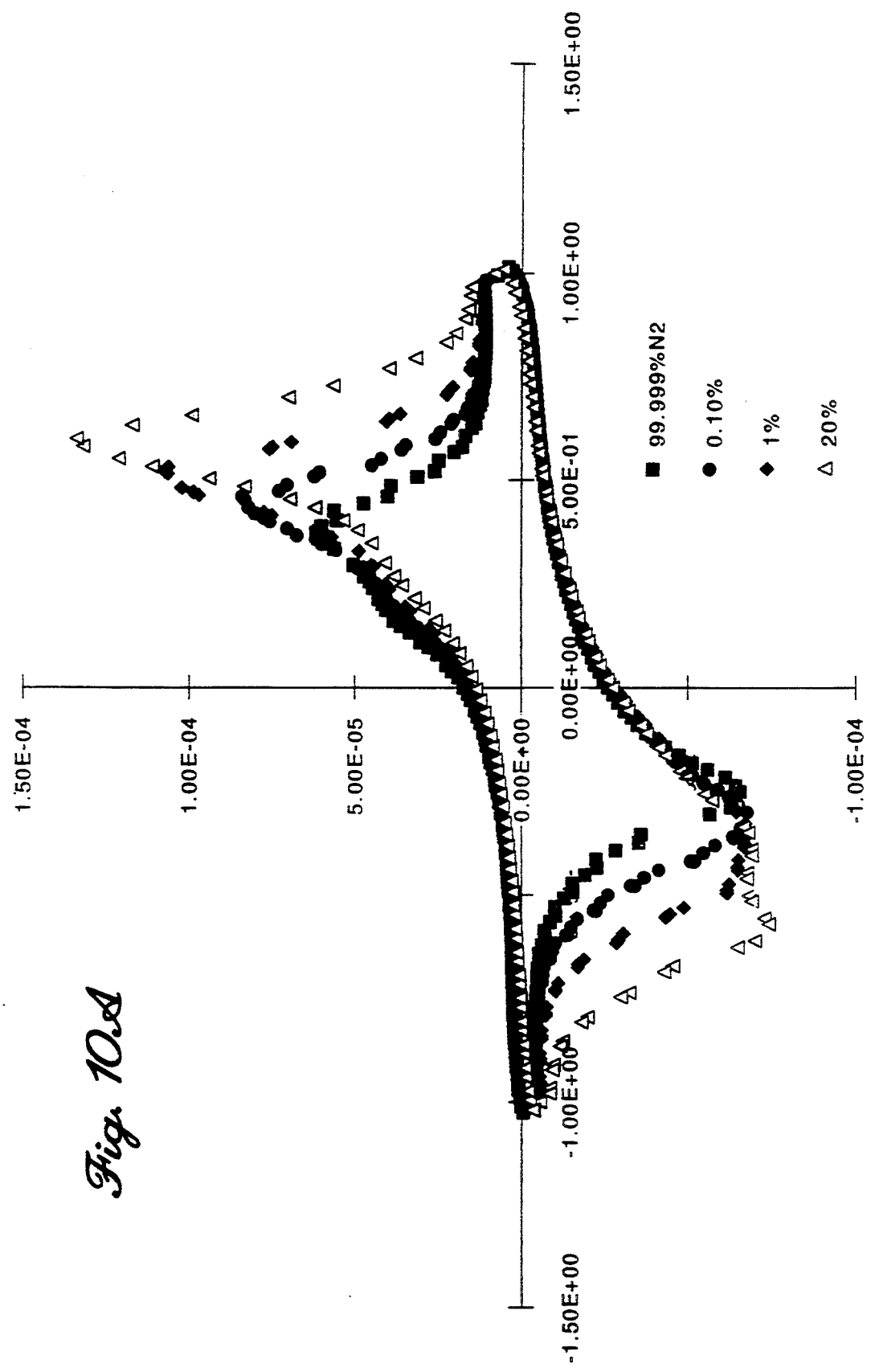
FIG. 10A illustrates the response of a sensor device in a voltage driven mode for different oxygen concentrations.
Figure 10B:
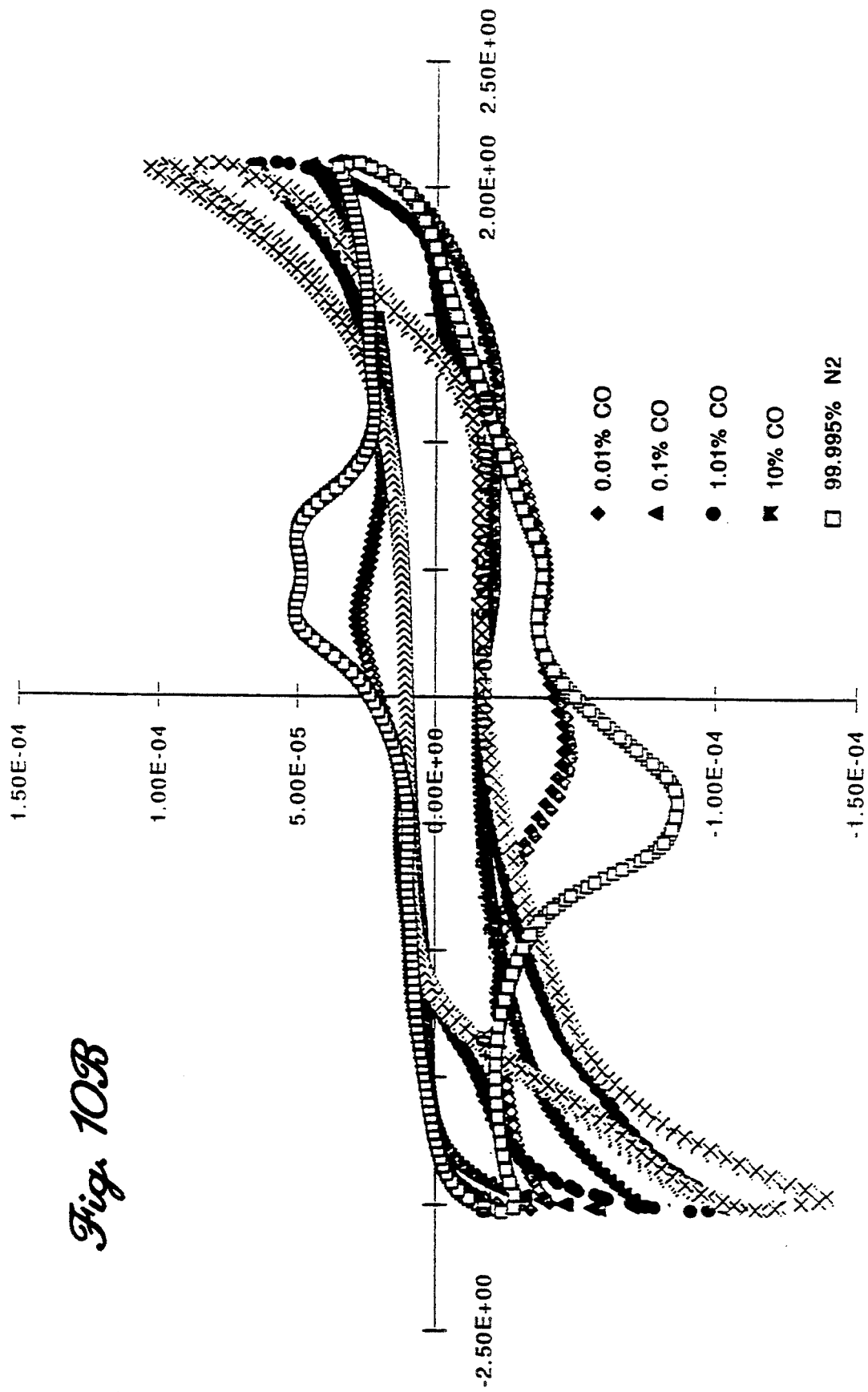
FIG. 10B shows a voltage driven sensor device response for different CO concentrations.
Figure 10E:
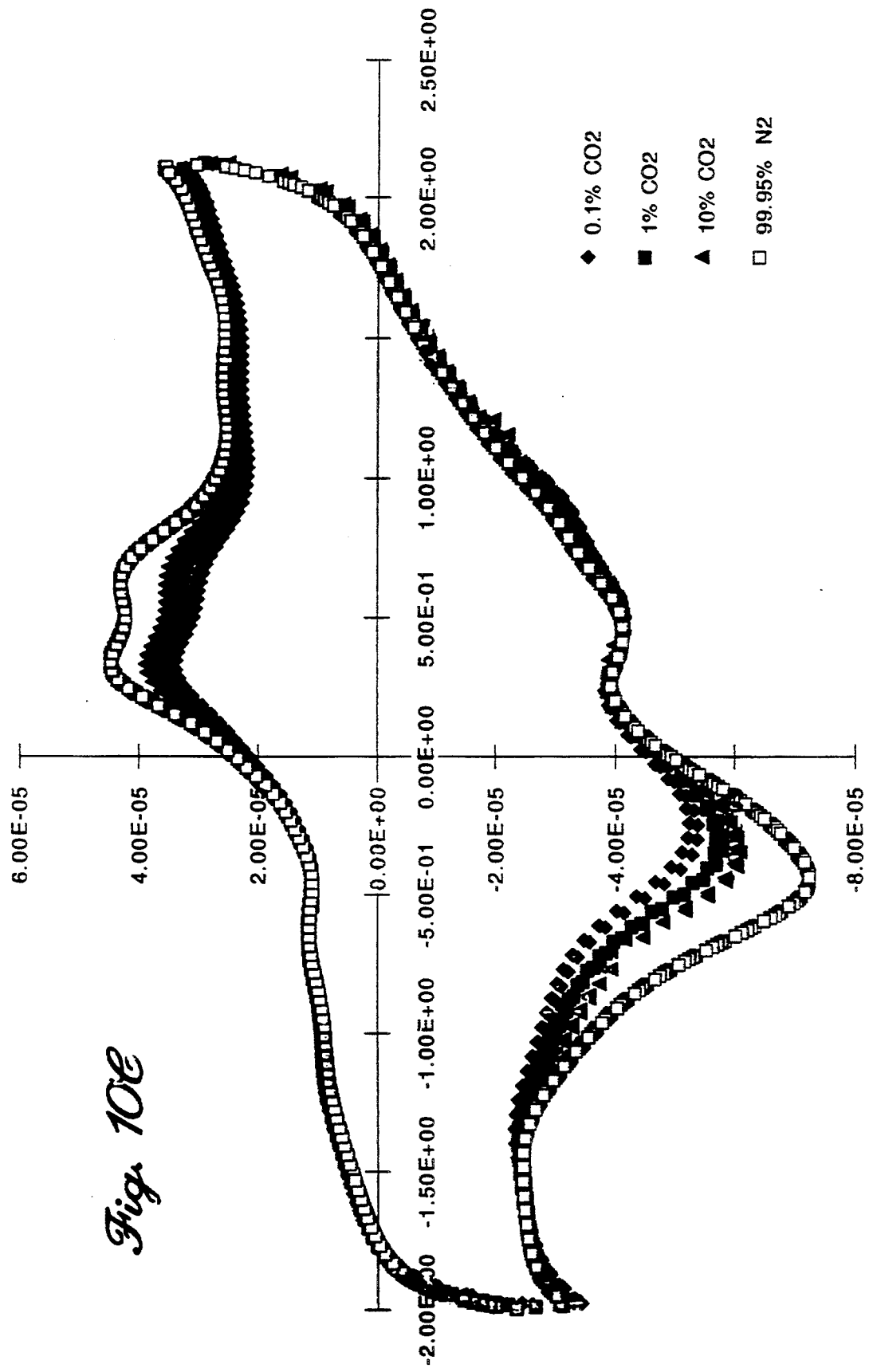
FIG. 10E shows a voltage driven sensor device response illustrating the nitrogen carrier gas recovery effect of the sensor for different recovery time periods.
Figure 10E:
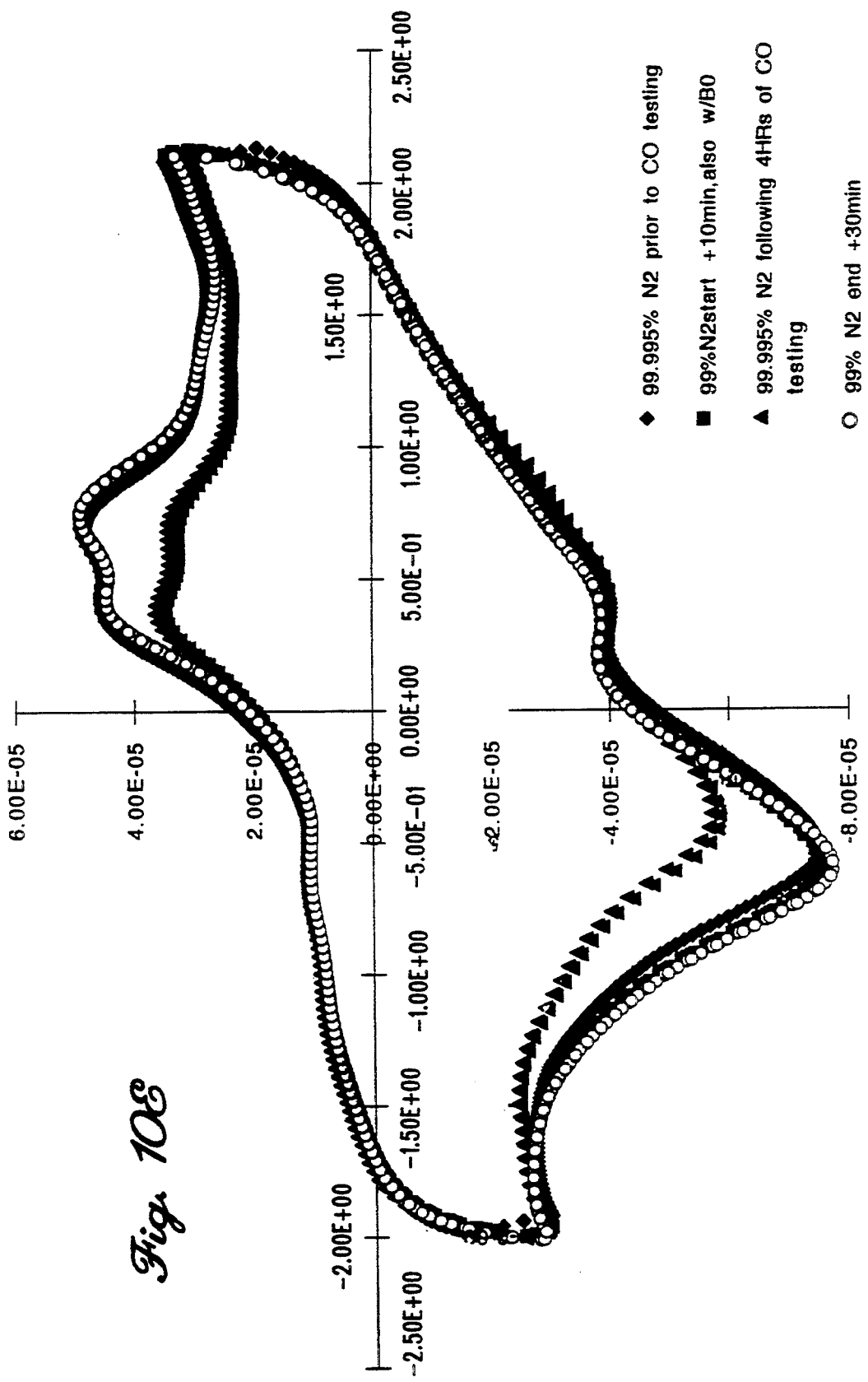
Figure 10H:
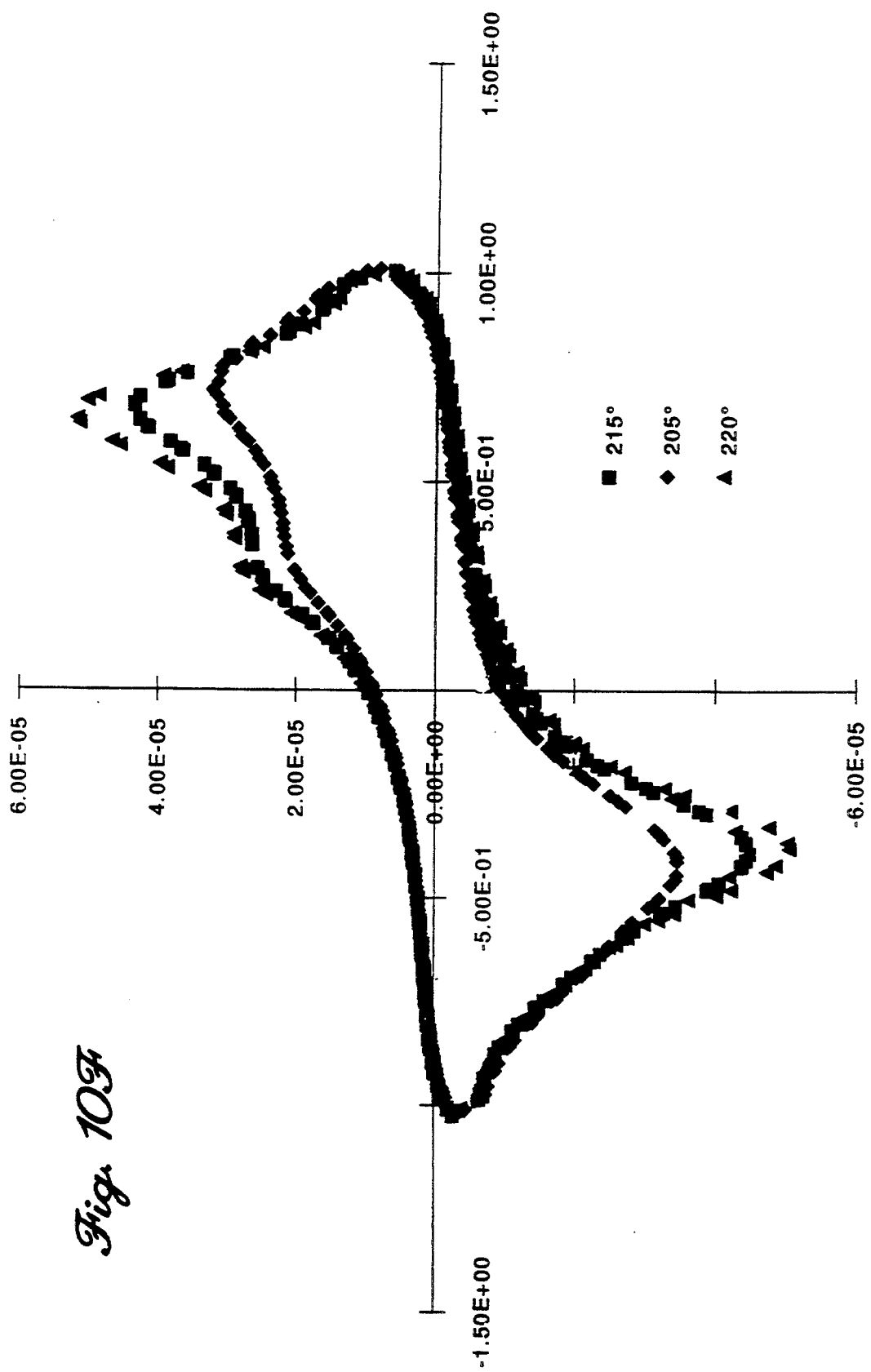
FIG. 10C shown a voltage driven sensor device response for different CO₂ concentrations.
FIG. 10D shows a voltage driven sensor device response for different methane concentrations.
FIG. 10F illustrates a voltage driven sensor device response for nitrogen gas at different sensor operating temperatures.
FIG. 10G shows a voltage driven sensor device response for different CO/CO₂ mixtures.
Figure 10E:
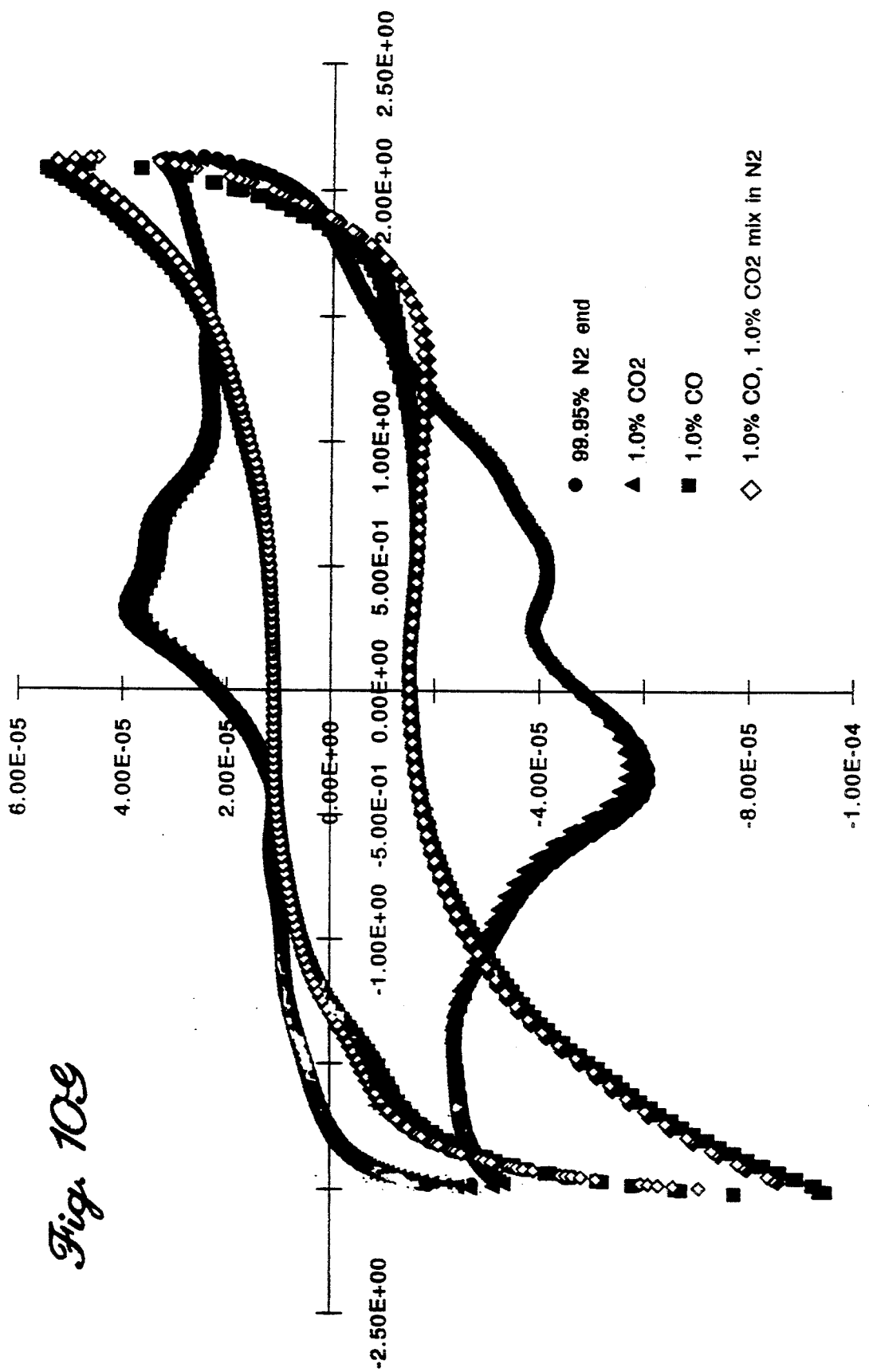

A series of voltage driven tests were performed using the gas sensor device. The device was placed in a quartz tube furnace, a power source coupled to the sensor, and a DC voltage was applied to the sensor device to obtain an output in DC amperes to define a closed loop curve. In a first test, the sensor device was heated to 250° C. and various gas mixtures of varying oxygen percentage were introduced. Upon applying the drive voltages characteristic signals were obtained as shown in FIG. 10A. In a second test, the sensor device was heated to 250° C. and various CO percentages were introduced. Upon applying the drive voltages, characteristic signals were obtained as shown in FIG. 10B. In a third test, the sensor device was heated to 250° C. and various $CO_2$ percentages were introduced. Upon applying the drive voltages, characteristic signals were obtained as shown in FIG. 10C. In a fourth test, the sensor device was heated to 250° C. and various methane concentrations were introduced. Upon applying the drive voltages, characteristic signals were obtained as shown in FIG. 10D. In a fifth test, the nitrogen gas recovery effect is evaluated under various test conditions illustrated in FIG. 10E. In a sixth test, an evaluation was performed of the sensor device for $N_2$ gas at different sensor operating temperatures (see FIG. 10F). In a seventh test, the sensor device was heated to 250° C. and various CO/-$CO_2$ mixtures were introduced. Upon applying the drive voltages, characteristic signals were obtained as shown in FIG. 10G.

EXAMPLE IV

Figure 12A:
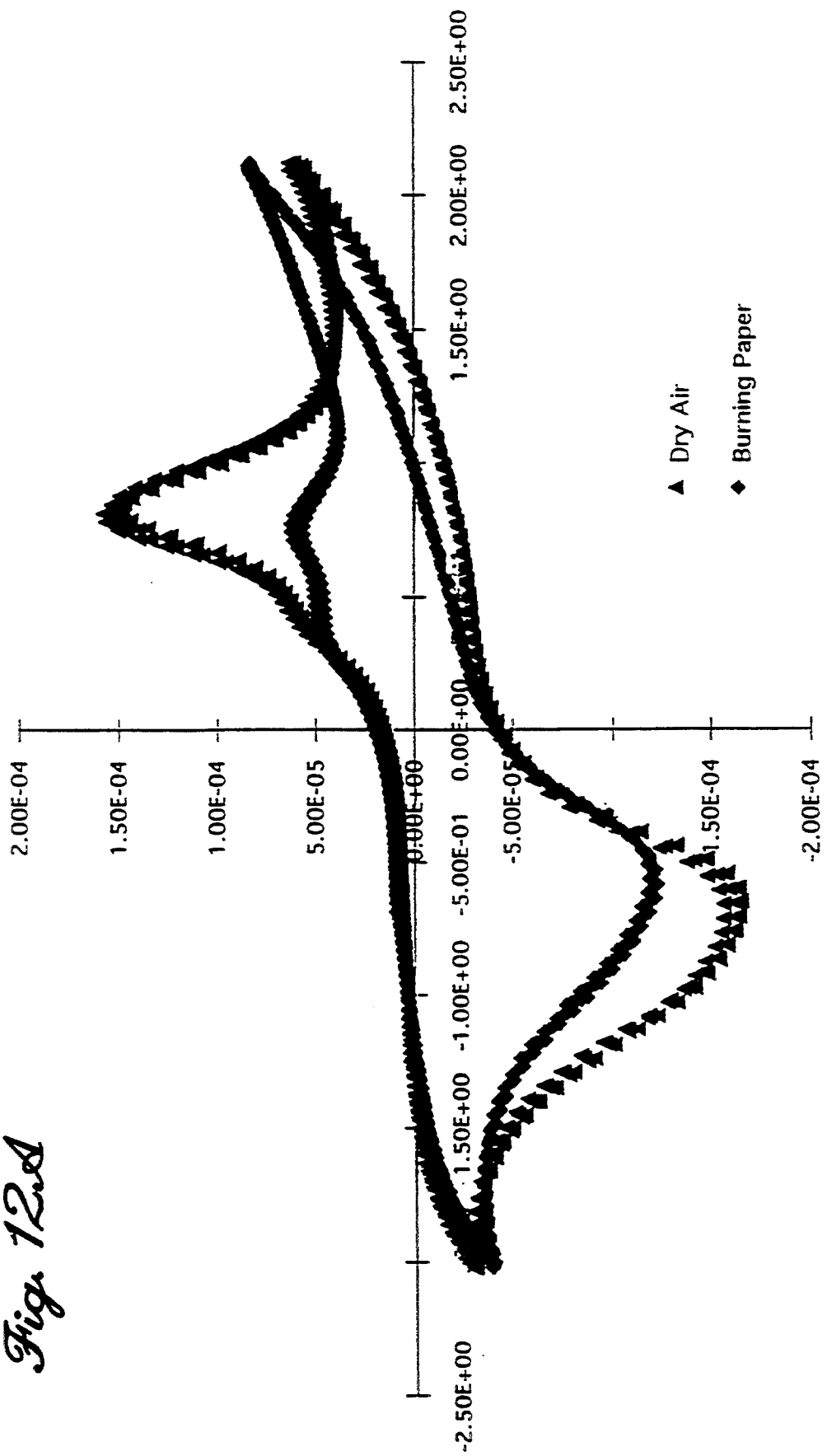
FIG. 12A illustrates the response of a sensor device in a voltage driven mode to fumes from burning paper.
Figure 12B:
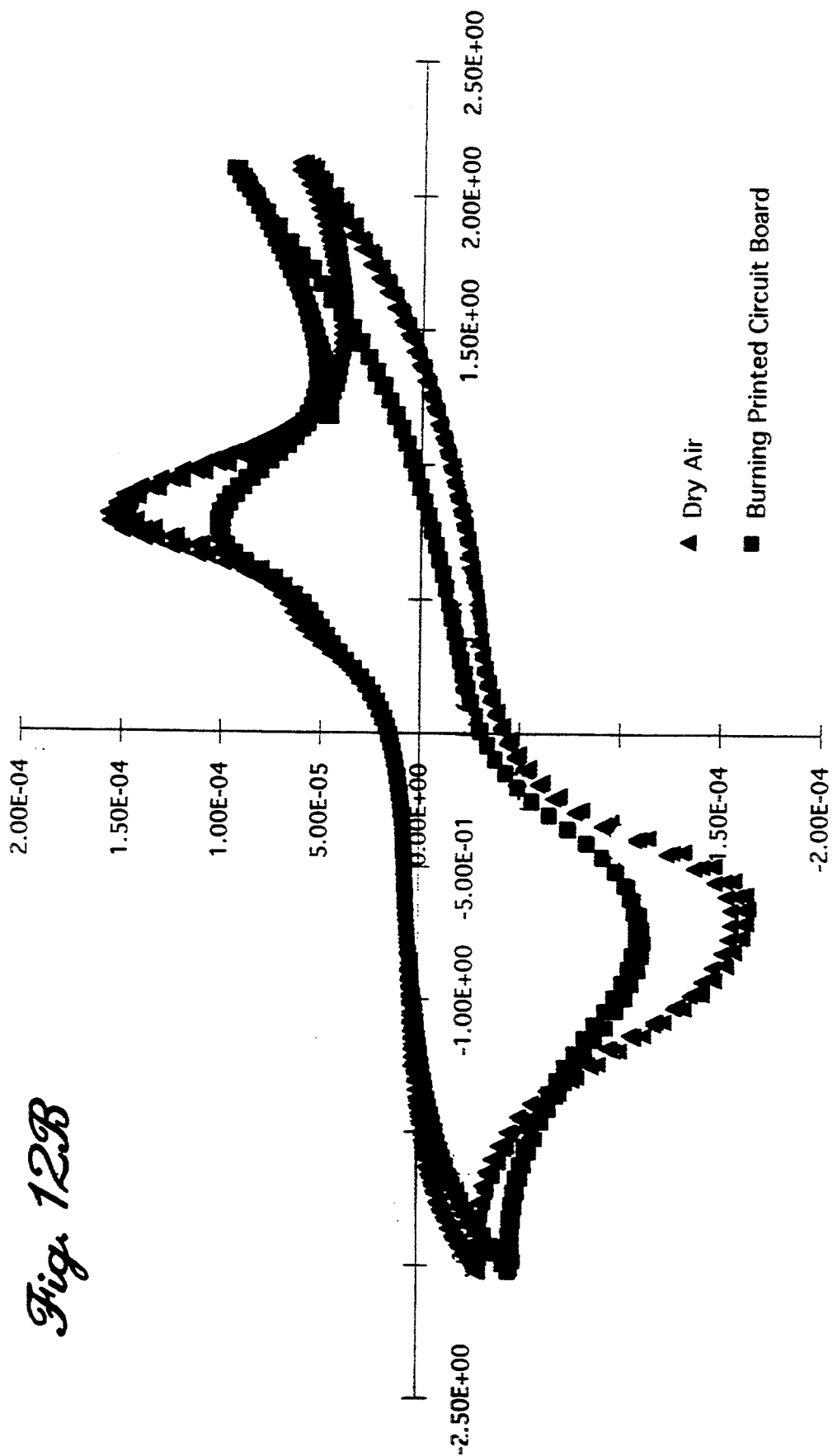
FIG. 12B illustrates a voltage driven sensor device response to fumes from a bunting electronic circuit board.
Figure 12C:
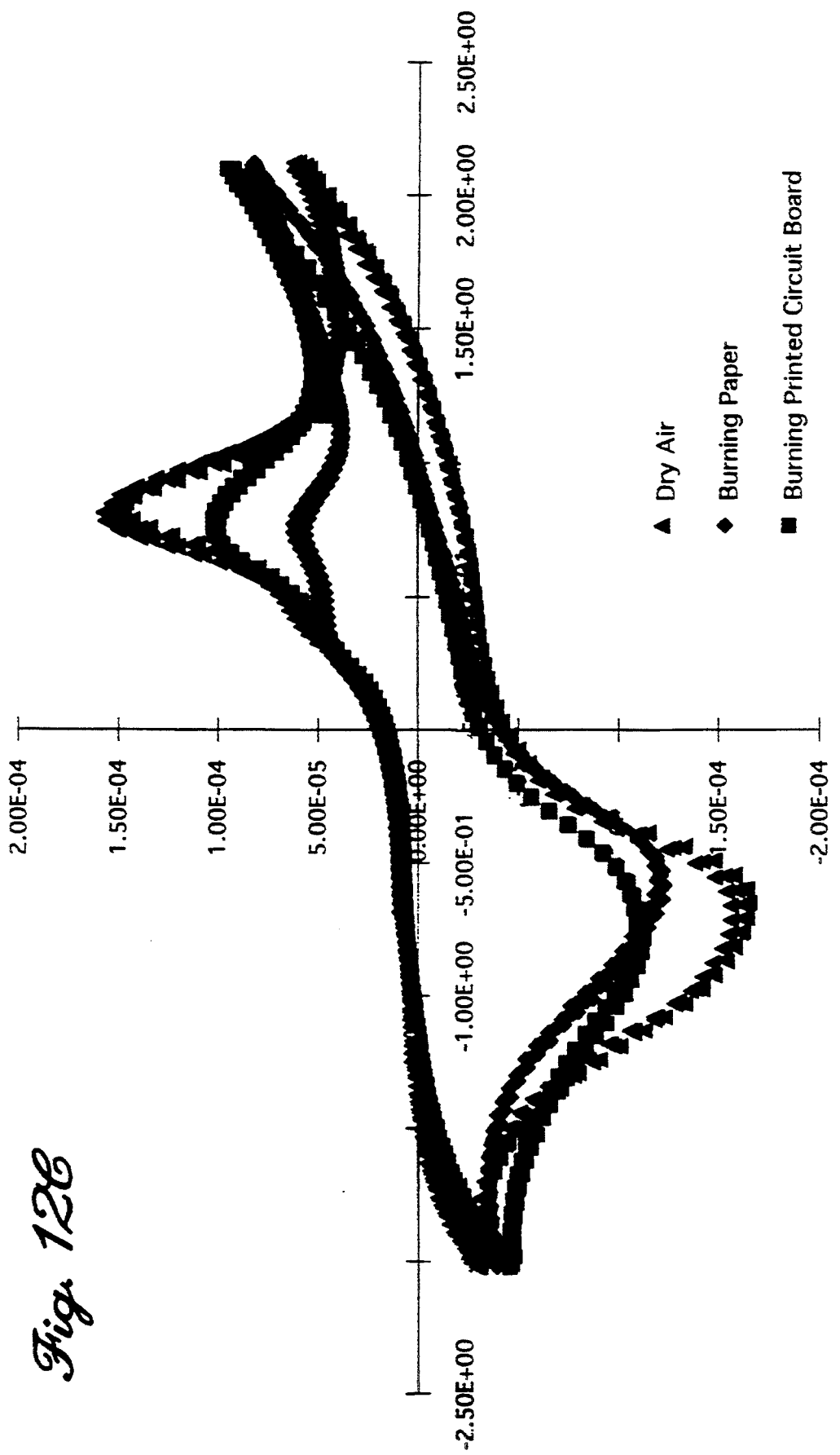
FIG. 12C shows a voltage driven mode for detection of burning PCB and paper.

Complex gas mixtures can also be analyzed qualitatively with great precision. It can, for example, be important to distinguish between burning paper and burning plastic due, in particular, to the toxic threat posed by the latter. In industrial applications the sensor device can advantageously be used to recognize the fumes of burning, or overheated, electronic circuit boards. Closed loop characteristic plots were generated in the manner described in Example III. In FIG. 12A is shown the characteristic voltage driven plot for burning paper which can be compared to the plot for a burning electronic circuit board in FIG. 12B, and burning PCB as well as paper in FIG. 12C.

While preferred embodiments of the invention have been shown and described, it will be clear to those skilled in the art that various changes and modifications can be made without departing from the invention in its broader aspects as set forth in the claims provided hereinafter.

APPENDIX OF COMPUTER SOFTWARE

```
on idle
   global timerInterval
   global aTimeHolder
   global WfileName
   global scannerStatus
   global powerStatus
   global ch1Status
   global ch2Status
   global ch3Status
   global ch4Status
   global ch5Status
   global ch6Status
   global ch7Status
   global ch8Status
   global ch9Status
   global ch10Status
   global ch1Parameter
   global ch2Parameter
   global ch3Parameter
   global ch4Parameter
   global ch5Parameter
   global ch6Parameter
   global ch7Parameter
   global ch8Parameter
   global ch9Parameter
   global ch10Parameter if powerStatus = "on"
   then
      open file WfileName
      read from file WfileName until empty
      set scroll of card field 2 to 0
      put empty into card field 1
      put empty into card field 2 repeat with outerLoop=1 to 1000
         repeat with XLine=1 to 60 if timerInterval= "hs"
```

```
then
  put the long time into aTimeHolder
  --no delay... acquire data as fast as possible
else --if hs is true then this ENTIRE section should be skipped if timerInterval= "5sec"
  then
    put the long time into aTimeHolder
    if length of aTimeHolder<8 then put 0 before aTimeHolder
    repeat until char 8 of aTimeHolder=0 or ¬
      char 8 of aTimeHolder=5
      put the long time into aTimeHolder
      if length of aTimeHolder<8 then put 0 before aTimeHolder
    end repeat
  else
  end if if timerInterval= "10sec"
  then
    put the long time into aTimeHolder
    if length of aTimeHolder<8 then put 0 before aTimeHolder
    repeat until char 8 of aTimeHolder=0
    put the long time into aTimeHolder
    if length of aTimeHolder<8 then put 0 before aTimeHolder
    end repeat
  else
  end if if timerInterval= "30sec"
  then
    put the long time into aTimeHolder
    if length of aTimeHolder<8 then put 0 before aTimeHolder
    repeat until char 8 of aTimeHolder=0 and ¬
      ¬(char 7 of aTimeHolder=3 or char 7 of aTimeHolder=0)
      put the long time into aTimeHolder
      if length of aTimeHolder<8 then put 0 before aTimeHolder
    end repeat
  else
  end if if timerInterval= "1min"
  then
    put the long time into aTimeHolder
    if length of aTimeHolder<8 then put 0 before aTimeHolder
    repeat until char 8 of aTimeHolder=0 and ¬
      char 7 of aTimeHolder=0
      put the long time into aTimeHolder
      if length of aTimeHolder<8 then put 0 before aTimeHolder
    end repeat
  else
  end if if timerInterval= "5min"
  then
    put the long time into aTimeHolder
    if length of aTimeHolder<8 then put 0 before aTimeHolder
    repeat until char 8 of aTimeHolder=0 and ¬
      char 7 of aTimeHolder=0 and ¬
      (char 5 of aTimeHolder=0 or char 5 of aTimeHolder=5)
      put the long time into aTimeHolder
      if length of aTimeHolder<8 then put 0 before aTimeHolder
    end repeat
  else
  end if if timerInterval= "30min"
  then
    put the long time into aTimeHolder
    if length of aTimeHolder<8 then put 0 before aTimeHolder
    repeat until char 8 of aTimeHolder=0 and ¬
```

```
        char 7 of aTimeHolder=0 and ¬
        char 5 of aTimeHolder=0 and ¬
        (char 4 of aTimeHolder=0 or char 4 of aTimeHolder=3)
        put the long time into aTimeHolder
        if length of aTimeHolder<8 then put 0 before aTimeHolder
      end repeat
   else
   end if if timerInterval= "60min"
   then
      put the long time into aTimeHolder
      if length of aTimeHolder<8 then put 0 before aTimeHolder
      repeat until char 8 of aTimeHolder=0 and ¬
        char 7 of aTimeHolder=0 and ¬
        char 5 of aTimeHolder=0 and ¬
        char 4 of aTimeHolder=0
        put the long time into aTimeHolder
        if length of aTimeHolder<8 then put 0 before aTimeHolder
      end repeat
   else
   end if end if --exit from hs if-loop test put outerLoop&&"/"&&XLine&&","&&aTimeHolder&&"," after card field 2 if scannerStatus= "on"
then            --TREAT LIKE FUNCTIONING SCANNER if   ch1Status="on"
   then
      Ieee "output 18;C1B1X"
      wait 10 ticks              -- 1 second settle time for relays
      if ch1Parameter="DCV" then Ieee "output 07;P99G1S3T4F0R0X"
      if ch1Parameter="ACV" then Ieee "output 07;P99G1S3T4F1R0X"
      if ch1Parameter="OHM" then Ieee "output 07;P99G1S3T4F2R0X"
      if ch1Parameter="DCA" then Ieee "output 07;P99G1S3T4F3R0X"
      if ch1Parameter="ACA" then Ieee "output 07;P99G1S3T4F4R0X"
      Ieee "enter 07"
      put the result into ResHolder
      Ieee "output 18;N1X"
      put ResHolder&&" "&&",1" into card field 1
      put ResHolder&&"," after card field 2
   else
   end if if   ch2Status="on"
   then
      Ieee "output 18;C2B2X"
      wait 10 ticks              -- 1 second settle time for relays
      if ch2Parameter="DCV" then Ieee "output 07;P99G1S3T4F0R0X"
      if ch2Parameter="ACV" then Ieee "output 07;P99G1S3T4F1R0X"
      if ch2Parameter="OHM" then Ieee "output 07;P99G1S3T4F2R0X"
      if ch2Parameter="DCA" then Ieee "output 07;P99G1S3T4F3R0X"
      if ch2Parameter="ACA" then Ieee "output 07;P99G1S3T4F4R0X"
      Ieee "enter 07"
      put the result into ResHolder
      Ieee "output 18;N2X"
      put ResHolder&&" "&&",2" into card field 1
      put ResHolder&&"," after card field 2
   else
   end if
```

```
if   ch3Status="on"
then
  Ieee "output 18;C3B3X"
  wait 10 ticks            -- 1 second settle time for relays
  if ch3Parameter="DCV" then Ieee "output 07;P99G1S3T4F0R0X"
  if ch3Parameter="ACV" then Ieee "output 07;P99G1S3T4F1R0X"
  if ch3Parameter="OHM" then Ieee "output 07;P99G1S3T4F2R0X"
  if ch3Parameter="DCA" then Ieee "output 07;P99G1S3T4F3R0X"
  if ch3Parameter="ACA" then Ieee "output 07;P99G1S3T4F4R0X"
  Ieee "enter 07"
  put the result into ResHolder
  Ieee "output 18;N3X"
  put ResHolder&&" "&&",3" into card field 1
  put ResHolder&&"," after card field 2
else
end if if   ch4Status="on"
then
  Ieee "output 18;C4B4X"
  wait 10 ticks            -- 1 second settle time for relays
  if ch4Parameter="DCV" then Ieee "output 07;P99G1S3T4F0R0X"
  if ch4Parameter="ACV" then Ieee "output 07;P99G1S3T4F1R0X"
  if ch4Parameter="OHM" then Ieee "output 07;P99G1S3T4F2R0X"
  if ch4Parameter="DCA" then Ieee "output 07;P99G1S3T4F3R0X"
  if ch4Parameter="ACA" then Ieee "output 07;P99G1S3T4F4R0X"
  Ieee "enter 07"
  put the result into ResHolder
  Ieee "output 18;N4X"
  put ResHolder&&" "&&",4" into card field 1
  put ResHolder&&"," after card field 2
else
end if if   ch5Status="on"
then
  Ieee "output 18;C5B5X"
  wait 10 ticks            -- 1 second settle time for relays
  if ch5Parameter="DCV" then Ieee "output 07;P99G1S3T4F0R0X"
  if ch5Parameter="ACV" then Ieee "output 07;P99G1S3T4F1R0X"
  if ch5Parameter="OHM" then Ieee "output 07;P99G1S3T4F2R0X"
  if ch5Parameter="DCA" then Ieee "output 07;P99G1S3T4F3R0X"
  if ch5Parameter="ACA" then Ieee "output 07;P99G1S3T4F4R0X"
  Ieee "enter 07"
  put the result into ResHolder
  Ieee "output 18;N5X"
  put ResHolder&&" "&&",5" into card field 1
  put ResHolder&&"," after card field 2
else
end if if   ch6Status="on"
then
  Ieee "output 18;C6B6X"
  wait 10 ticks            -- 1 second settle time for relays
  if ch6Parameter="DCV" then Ieee "output 07;P99G1S3T4F0R0X"
  if ch6Parameter="ACV" then Ieee "output 07;P99G1S3T4F1R0X"
  if ch6Parameter="OHM" then Ieee "output 07;P99G1S3T4F2R0X"
  if ch6Parameter="DCA" then Ieee "output 07;P99G1S3T4F3R0X"
  if ch6Parameter="ACA" then Ieee "output 07;P99G1S3T4F4R0X"
  Ieee "enter 07"
  put the result into ResHolder
  Ieee "output 18;N6X"
  put ResHolder&&" "&&",6" into card field 1
  put ResHolder&&"," after card field 2
else
end if
```

```
if   ch7Status="on"
then
  Ieee "output 18;C7B7X"
  wait 10 ticks              -- 1 second settle time for relays
  if ch7Parameter="DCV" then Ieee "output 07;P99G1S3T4F0R0X"
  if ch7Parameter="ACV" then Ieee "output 07;P99G1S3T4F1R0X"
  if ch7Parameter="OHM" then Ieee "output 07;P99G1S3T4F2R0X"
  if ch7Parameter="DCA" then Ieee "output 07;P99G1S3T4F3R0X"
  if ch7Parameter="ACA" then Ieee "output 07;P99G1S3T4F4R0X"
  Ieee "enter 07"
  put the result into ResHolder
  Ieee "output 18;N7X"
  put ResHolder&&" "&&",7" into card field 1
  put ResHolder&&"," after card field 2
else
end if if   ch8Status="on"
then
  Ieee "output 18;C8B8X"
  wait 10 ticks              -- 1 second settle time for relays
  if ch8Parameter="DCV" then Ieee "output 07;P99G1S3T4F0R0X"
  if ch8Parameter="ACV" then Ieee "output 07;P99G1S3T4F1R0X"
  if ch8Parameter="OHM" then Ieee "output 07;P99G1S3T4F2R0X"
  if ch8Parameter="DCA" then Ieee "output 07;P99G1S3T4F3R0X"
  if ch8Parameter="ACA" then Ieee "output 07;P99G1S3T4F4R0X"
  Ieee "enter 07"
  put the result into ResHolder
  Ieee "output 18;N8X"
  put ResHolder&&" "&&",8" into card field 1
  put ResHolder&&"," after card field 2
else
end if if   ch9Status="on"
then
  Ieee "output 18;C9B9X"
  wait 10 ticks              -- 1 second settle time for relays
  if ch9Parameter="DCV" then Ieee "output 07;P99G1S3T4F0R0X"
  if ch9Parameter="ACV" then Ieee "output 07;P99G1S3T4F1R0X"
  if ch9Parameter="OHM" then Ieee "output 07;P99G1S3T4F2R0X"
  if ch9Parameter="DCA" then Ieee "output 07;P99G1S3T4F3R0X"
  if ch9Parameter="ACA" then Ieee "output 07;P99G1S3T4F4R0X"
  Ieee "enter 07"
  put the result into ResHolder
  Ieee "output 18;N9X"
  put ResHolder&&" "&&",9" into card field 1
  put ResHolder&&"," after card field 2
else
end if if   ch10Status="on"
then
  Ieee "output 18;C10B10X"
  wait 10 ticks              -- 1 second settle time for relays
  if ch10Parameter="DCV" then Ieee "output 07;P99G1S3T4F0R0X"
  if ch10Parameter="ACV" then Ieee "output 07;P99G1S3T4F1R0X"
  if ch10Parameter="OHM" then Ieee "output 07;P99G1S3T4F2R0X"
  if ch10Parameter="DCA" then Ieee "output 07;P99G1S3T4F3R0X"
  if ch10Parameter="ACA" then Ieee "output 07;P99G1S3T4F4R0X"
  Ieee "enter 07"
  put the result into ResHolder
  Ieee "output 18;N10X"
  put ResHolder&&" "&&",10" into card field 1
  put ResHolder&&"," after card field 2
else
end if
```

```
      else            --scanner = "off" TREAT LIKE NORMAL 1 CHANNEL DMM
        wait 1 secs --68030 too fast,delay or gets in 2 readings on 00
        Ieee "enter 07"    -- just pull number from dmm
        put the result into ResHolder
        put ResHolder&&" " into card field 1
        put ResHolder&&"," after card field 2 end if put return after card field 2 write line XLine of card field 2 to file WfileName
      write return to file WfileName if XLine>=5 then set the scroll of card field 2 to ((XLine-4)*12)

end repeat
    wait 2 secs
    put empty into card field 2
    set scroll of card field 2 to 0
  end repeat close file WfileName put empty into card field 2  --clear the field for more data end if
end idle
```

CODE FOR VIRTUAL CONTROLLER

```
on idle
  global timerInterval
  global aTimeHolder
  global WfileName
  global powerStatus
  global OhmStatus
  global IndStatus
  global CapStatus if powerStatus = "on"
then
  open file WfileName
  read from file WfileName until empty
  set scroll of card field 1 to 0
  put empty into card field 1
  put empty into card field 2 repeat with outerLoop=1 to 1000
    repeat with XLine=1 to 60 if timerInterval= "hs"
      then
        put the long time into aTimeHolder
        --no delay at all... collect as fast as possible.
        else--next section should be skipped if hs is true if timerInterval= "5sec"
        then
          put the long time into aTimeHolder
          if length of aTimeHolder<8 then put 0 before aTimeHolder
          repeat until char 8 of aTimeHolder=0 or ¬
            char 8 of aTimeHolder=5
```

```
      put the long time into aTimeHolder
      if length of aTimeHolder<8 then put 0 before aTimeHolder
   end repeat
else
end if if timerInterval= "10sec"
then
   put the long time into aTimeHolder
   if length of aTimeHolder<8 then put 0 before aTimeHolder
   repeat until char 8 of aTimeHolder=0
      put the long time into aTimeHolder
      if length of aTimeHolder<8 then put 0 before aTimeHolder
   end repeat
else
end if if timerInterval= "30sec"
then
   put the long time into aTimeHolder
   if length of aTimeHolder<8 then put 0 before aTimeHolder
   repeat until char 8 of aTimeHolder=0 and ¬
     (char 7 of aTimeHolder=3 or char 7 of aTimeHolder=0)
      put the long time into aTimeHolder
      if length of aTimeHolder<8 then put 0 before aTimeHolder
   end repeat
else
end if if timerInterval= "1min"
then
   put the long time into aTimeHolder
   if length of aTimeHolder<8 then put 0 before aTimeHolder
   repeat until char 8 of aTimeHolder=0 and ¬
      char 7 of aTimeHolder=0
      put the long time into aTimeHolder
      if length of aTimeHolder<8 then put 0 before aTimeHolder
   end repeat
else
end if if timerInterval= "5min"
then
   put the long time into aTimeHolder
   if length of aTimeHolder<8 then put 0 before aTimeHolder
   repeat until char 8 of aTimeHolder=0 and ¬
      char 7 of aTimeHolder=0 and ¬
      (char 5 of aTimeHolder=0 or char 5 of aTimeHolder=5)
      put the long time into aTimeHolder
      if length of aTimeHolder<8 then put 0 before aTimeHolder
   end repeat
else
end if if timerInterval= "30min"
then
   put the long time into aTimeHolder
   if length of aTimeHolder<8 then put 0 before aTimeHolder
   repeat until char 8 of aTimeHolder=0 and ¬
      char 7 of aTimeHolder=0 and ¬
      char 5 of aTimeHolder=0 and ¬
      (char 4 of aTimeHolder=0 or char 4 of aTimeHolder=3)
      put the long time into aTimeHolder
      if length of aTimeHolder<8 then put 0 before aTimeHolder
   end repeat
else
end if if timerInterval= "60min"
then
```

```
              put the long time into aTimeHolder
              if length of aTimeHolder<8 then put 0 before aTimeHolder
              repeat until char 8 of aTimeHolder=0 and ¬
                char 7 of aTimeHolder=0 and ¬
                char 5 of aTimeHolder=0 and ¬
                char 4 of aTimeHolder=0
                put the long time into aTimeHolder
                if length of aTimeHolder<8 then put 0 before aTimeHolder
              end repeat
            else
            end if end if -- end of hs test loop put outerLoop&&"/"&&XLine&&","&&aTimeHolder&&"," ¬
        after card field 1

--no scanner ; TREAT LIKE NORMAL 1 CHANNEL GenRad
        --wait 1 secs --68030 too fast,delay or gets in 2 readings on 00

Ieee "output 03;P2S0M3D2R5x0T1G0Q0X4X" -- ohm reading
        Ieee "enter 03"
        put the result into ResHolder
        put ResHolder&&" " into card field 2
        put ResHolder&&"," after card field 1

Ieee "output 03;P2S0M2D2R5x0T1G0Q0X4X" -- capacitor reading
        Ieee "enter 03"
        put the result into ResHolder
        put ResHolder&&" " into card field 2
        put ResHolder&&"," after card field 1 put return after card field 1 write line XLine of card field 1 to file WfileName
        write return to file WfileName if XLine>=5 then set the scroll of card field 1 to ¬
        ((XLine-4)*12)

end repeat
      wait 2 secs
      put empty into card field 1
      set scroll of card field 1 to 0
    end repeat close file WfileName put empty into card field 1   --clear the field for more data else end if
end idle
```

```
/*============================*/
/*      NETS         */
/*                  */
/*  a product of the    */
/*    Software Technology Branch */
/* NASA, Johnson Space Center */
/*                  */
/* authors:              */
/*    Paul Baffes     */
/*    Steve Bayer     */
/*    Bryan Dulock    */
/*    Linda Jensen    */
/*    Chris Ortiz     */
/*    Gary Riley      */
/*    Robert Shelton  */
/*    Todd Phillips   */
/*============================*/

/*
------------------------------------------------------------------
```

This is the main module for the neural net. All of the main code plus documentation on the system features lives here.

A note on nomenclature: Most of the routine calls which you will see in the code throughout these files will be "prefixed" by some letters and an underscore. That is one of my conventions for indicating which file contains the code for the subroutine in question. Because I have several files, this makes tracing problems and debugging files easier to accomplish.

This file is one of 14 source files which make up the back propagation code. These files are the following:

```
    activate.c      semi-linear activation function
    buildnet.c
    compile.c
    convert.c       conversion routines, conversion routines
    layer.c         layer manipulation and creation
    lnrate.c
    net.c           net manipulation, learning, propagation
    netio.c         I/O routines, file handlers
    netmain.c       main routines, menus, user interface
    pairs.c
    prop.c
    shownet.c
    scaleio.c                   Scales IO pairs and Input files
    teach.c
    weights.c       weights manipulation and creation
```

All of these are covered in detail in the respective files. The prefix codes for each of the files are as follows:

```
    activate.c      "A_"
    buildnet.c      "B_"
    compile.c       "CC_"
    convert.c       "C_"
    dribble.c       "D_"
    net.c           "N_"
    netio.c         "IO_"
    netmain.c       *NONE-
    pairs.c         "PA_"
```

```
    parser.c        "PS_"
    prop.c          "P_"
    layer.c         "L_"
    lnrate.c        "LR_"
    shownet.c       "S_"
    scaleio.c                    "SC_"
    teach.c         "T_"
    weights.c       "W_"
    sysdep.c        "sys_"  (system dependent code)
```

The rest of this file is organized into the folloing groups:

(1) include files
(2) externed functions
(3) global variables
(4) subroutines

------------------------------------------------------------
*/

/*
------------------------------------------------------------
INCLUDE FILES
------------------------------------------------------------
*/
include "common.h"
include "netio.h"
include "weights.h"
include "layer.h"
include "net.h"

/* there are two versions of the main loop -- one for the text based interface and one for macintosh */ if !MAC_GRAPH
/*
------------------------------------------------------------
EXTERNED FUNCTIONS
------------------------------------------------------------
*/
extern void         A_initialize();

extern Net    *B_create_net();
extern Net    *B_free_net();

extern void   N_query_net();
extern int    N_reset_wts();
extern void   N_save_wts();
extern Layer  *N_get_layer();

extern void T_signal_handle ();
extern void  T_teach_net();
extern void T_display_error_stats();

extern void   S_show_weights();
extern void   S_show_biases();
extern void   S_show_net();

extern float  IO_my_get_float();
extern int    IO_my_get_int();
extern int    IO_get_default_int();
extern int    IO_get_num_cycles();
extern void   IO_my_get_string();

```
extern void   IO_set_filenames();
extern void   IO_get_io_name();
extern void   IO_get_wts_name();
extern void   IO_print();

extern void   PA_initialize();
extern void   PA_setup_iopairs();
extern void   PA_reset_iopairs();
extern void   PA_randomize_file();
extern void   PA_done_with_workfile();

extern void   D_initialize();
extern void   D_dribble_status();

extern Sint   C_float_to_Sint();
extern void   L_modify_learning();
extern void   sys_init_rand();
extern void       sys_SetUpVBLTask();
extern void       sys_RemoveVBLTask();
extern void   CC_create_delivery();
```

/*
---
GLOBAL VARIABLES
---
Next come the global variables, declared in other routines, which
need to be referenced here. In general I tried to keep the number
of globals to a minimum since they can be messy, but many of the
io functions needed to keep "state" variables for the lifetime of
the program execution. Examples are the default file names which
are used when prompting the user. These names are read here, and
referenced in net.c as well as netio.c, and thus I needed to be
able to pass them around. I could have simply left them as global
values and referenced them as needed, but instead I passed them
explicitly to the non-io routines that needed them. I could just
as easily have declared them here and made them external to the
io package, but since file names and IO are so intimately tied, I
thought it more logical to declare these variables with the other
IO code.
---

*/
```
extern char   net_config[];       /* these three from netio.c */
extern char   net_iop[];
extern char   net_fwt[];
extern char   net_pwt[];
extern char   no_interrupt;
extern char   IO_str[MAX_LINE_SIZE];

static Net *the_net;     /* variable which holds ptr to the net */
                         /* (global to this netmain routine only) */
```

/*
===
ROUTINES IN NETMAIN.C
===

```
/*
The routines in this file are grouped below by function.  NO ROUTINES
ARE PREFIXED IN THIS FILE.

The main routine is just below.  It basically amounts to a read-eval-
print loop, much like an interpreter. After initialization, this code
loops forever, calling "print_menu", "read_choice", and then
"evaluate".  The only other routine is a "check_net_ptr" routine
used during evaluate to verify that a valid net exists before
attempting some operation.
========================================================================
*/ main()
{
  void  initialize(), print_menu(), evaluate(), cleanup();
  char  read_choice();
  char  c;

#if LSPEED
        sys_SetUpVBLTask();
endif signal (SIGINT, T_signal_handle);

initialize();
  print_menu();
  while (TRUE) {
    c = read_choice();
     if (c == 'q') {
      cleanup();
      break;
     }
     evaluate(c);
  }
#if LSPEED
        sys_RemoveVBLTask();
endif }  /* main */ void initialize()
/*
-----------------------------------------------------------------
This is the initialization routine for the main program. Much
 of what the program is able to do is assumed here. For example
 I have assumed (for now) that we will be dealing with only one
 net at a time (even though I have made allowances in the NET
 structure for multiple nets).  Thus, this guy only initializes
 the one global 'the_net' variable.  This would need changing
 in the future if more nets were added.
Note also that the system random number generator is setup here
 This is significant since IT MAY NOT BE PORTABLE.
-----------------------------------------------------------------
*/
{
  the_net = NULL;
#if USE_SCALED_INTS
```

What is claimed is:

1. A device for sensing gases and including an electrical circuit portion therein having a plurality of layers, comprising;
   a substrate layer;
   a reference electrode source of anions disposed on said substrate layer, said reference electrode source of anions consisting essentially of a nonstoichiometric chemical compound for diffusing oxygen anions there through;
   a lower electrical reference electrode coupled to said reference electrode source of anions;
   a solid electrolyte coupled to said lower reference electrode, said solid electrolyte enabling diffusion of ions there through; and
   an upper catalytically active electrical electrode coupled to said solid electrolyte with electrical voltage applied between said lower electrical reference electrode and said upper electrical electrode with said reference electrode source of anions being disposed outside said plurality of layers comprised of said lower electrical reference electrode, said solid electrolyte and said upper electrical electrode.

2. The device as defined in claim 1 wherein said chemical compound is selected from the group consisting of Ni/NiO, Cd/CdO, Zn/ZnO, Ca/CaO, Co/CoO, Cu/CuO, Fe/FeO, V/VO, Ta/Ta$_2$O$_2$, Cr/CrO, Ni/NiS, Zn/Zns and mixtures thereof.

3. The device as defined in claim 1 wherein said chemical compound consists essentially of a cation rich binary compound.

4. The device as defined in claim 1 wherein said chemical compound is selected from the group consisting of a phosphide, an oxide, a selenide, a telluride and a sulfide.

5. The device as defined in claim 1 wherein said lower electrical reference electrode is selected from the group consisting of Pt, Cu, Ag and Pd.

6. The device as defined in claim 1 wherein said solid electrolyte consists essentially of an electrolyte which allows diffusion of particular ions of interest.

7. The device as defined in claim 6 wherein said particular ions of interest are selected from the group consisting of oxygen, sulfur, nitrogen, chlorine, fluorine and phosphorous.

8. The device as defined in claim 1 wherein said solid electrolyte is selected from the group consisting of yttria doped ZrO$_2$, CeO$_2$ and Bi$_2$O$_3$.

9. The device as defined in claim 1 wherein said upper catalytically active electrode is selected from the group consisting of Pt, Ru, Rh, Os, Ir, Pd and Au.

10. A device for sensing gases and including an electrical circuit portion therein having a plurality of layers, comprising:
    a substrate layer;
    layer means for establishing a reference source of anions;
    a lower electrical reference electrode coupled to said layer means;
    a solid electrolyte coupled to said lower electrical reference electrode, said solid electrolyte for diffusing ions of said reference gas there through; and
    an upper catalytically active electrical electrode coupled to said solid electrolyte with an electrical voltage applied between said lower electrical reference electrode and said upper electrical electrode with said layer means being disposed outside said plurality of layers comprised of said lower electrical reference electrode, said solid electrolyte and said upper electrical electrode.

11. The device as defined in claim 10 wherein said layer means consists essentially of a nonstoichiometric compound for providing said source of anions.

12. The device as defined in claim 11 wherein said nonstoichiometric compound is selected from the group consisting of an oxide, a sulfide, a phosphide, a selenide and a telluride.

13. The device as defined in claim 12 wherein said nonstoichiometric compound consists essentially of an anion deficient compound.

14. The device as defined in claim 10 wherein said lower electrical reference electrode is selected from the group consisting of Pt, Cu, Ag and Pd.

15. The device as defined in claim 10 wherein said upper catalytically active electrical electrode is selected from the group consisting of Pt, Ru, Rh, Os, Ir, Pd and Au.

16. A method of sensing a gas, comprising the steps of:
    (a) coupling a voltage source to a gas sensor device including an electrical circuit portion having a plurality of layers, comprised of:
        (1.) a substrate layer;
        (2.) a reference electrode source of anions including a nonstoichiometric compound for providing said anions and disposed on said substrate layer;
        (3.) a lower electrical reference electrode coupled to said reference electrode source of anions disposed on said substrate layer and said lower electrical reference electrode coupled to the voltage source;
        (4.) a solid electrolyte coupled to said lower reference electrode, said solid electrolyte diffusing ions there through; and
        (5.) an upper catalytically active electrical electrode coupled to said solid electrolyte with voltage from the voltage source applied between said lower electrical reference electrode and said upper electrical electrode and said reference electrode source of anions being disposed outside said plurality of layers comprised of said lower electrical reference electrode, said solid electrolyte and said upper electrical electrode.
    (b) during performing the method, applying a varying voltage from said voltage supply to said gas sensor device; and
    (c) collecting an output electrical signal from said gas sensor device wherein said output electrical signal is characteristic of said gas.

17. The method as defined in claim 16 wherein the varying voltage is applied to form a closed loop for said output electrical signal.

18. The method as defined in claim 16 wherein said step (a) further includes the step of inducing catalytic reactions of the gas at said upper catalytically active electrode.

19. The method as defined in claim 16 wherein said gas sensor device includes a heating layer for performing the step of heating said gas sensor device during use.

20. The method as defined in claim 19 wherein said heating layer further acts to carry out sensing of the temperature of said gas sensor device.

* * * * *